United States Patent [19]

Matsuo et al.

[11] Patent Number: 5,321,032
[45] Date of Patent: Jun. 14, 1994

[54] PEPTIDE COMPOUNDS AND PHARMACEUTICAL COMPOSITIONS THEREOF

[75] Inventors: Masaaki Matsuo, Toyonaka; Daijiro Hagiwara, Moriguchi; Hiroshi Miyake, Kyoto, all of Japan

[73] Assignee: Fujisawa Pharmaceutical Co., Ltd., Osaka, Japan

[21] Appl. No.: 916,853

[22] PCT Filed: Feb. 12, 1991

[86] PCT No.: PCT/JP91/00167
§ 371 Date: Aug. 12, 1992
§ 102(e) Date: Aug. 12, 1992

[87] PCT Pub. No.: WO91/12266
PCT Pub. Date: Aug. 22, 1991

[30] Foreign Application Priority Data

Feb. 15, 1990 [JP] Japan .................................. 2-34568

[51] Int. Cl.$^5$ ............... A61K 37/00; A61K 31/45; A61K 31/415; A61K 31/405; C07D 209/20; C07D 403/12; C07D 401/12; C07K 5/00
[52] U.S. Cl. ....................... 514/308; 514/18; 514/357; 514/414; 514/397; 514/419; 514/405; 530/331; 546/148; 546/264; 548/312.1; 548/453; 548/495
[58] Field of Search ............ 548/495, 312.1, 453; 546/148, 264; 530/331; 514/308, 357, 414, 397, 419, 405, 18

[56] References Cited

FOREIGN PATENT DOCUMENTS 0284942 10/1988 European Pat. Off. .
333174 3/1989 European Pat. Off. .
1-287095 11/1989 Japan .
9100167 4/1991 PCT Int'l Appl. .

*Primary Examiner*—David B. Springer
*Attorney, Agent, or Firm*—Oblon, Spivak, McClelland, Maier & Neustadt

[57] ABSTRACT

A tachykinin-antagonistic compound of the following general formula:

$$R^1-A^1-D-Trp(R^2)-A^2-R^3$$

[wherein
R$^1$ is hydrogen or amino-protective group
R$^2$ is amino-protective group
R$^3$ is ar(lower)alkoxy or N-(lower)alkyl or N-ar(lower)alkylamino
A$^1$ is single bond or one amino acid residue
A$^2$ is one amino acid residue other than Phe.]
or the salt thereof.

2 Claims, No Drawings

PEPTIDE COMPOUNDS AND PHARMACEUTICAL COMPOSITIONS THEREOF

FIELD OF ART

The present invention relates to a new peptide compound and the salt thereof, and more precisely, to a new peptide compound and the salt thereof which has a pharmaceutical activity such as tachykinin antagonism, especially substance P compound antagonism, neurochinin A antagonism, neurochinin B antagonism, and the like, and the process for the preparation of the above compound and tachykinin antagonism agent which contain the above compound as an active ingredient.

BACKGROUND OF ART

The object of the present invention is to provide a new and useful peptide compound and the salt thereof which has a pharmaceutical activity such as tachykinin antagonism, especially substance P compound antagonism, neurochinin A antagonism, neurochinin B antagonism, and the like.

The another object of the present invention is to provide a process for the preparation of the above peptide compound and the salt thereof.

The further object of the present invention is to provide a tachykinin antagonism agent which contains the above peptide compound or the salt thereof as an active ingredient.

The still further object of the present invention is to provide a use of the above peptide compound or the salt thereof as a tachykinin antagonism agent, especially substance P antagonism agent, neurochinin A antagonism agent, neurochinin B antagonism agent, and the like which is useful for therapeutics or prevention of tachykinin interstitial diseases of human or animals such as respiratry diseases (e.g., asthma, bronchitis, thiniris, cough, expectoration, etc.), ophthalmic diseases (e.g., conjunctivitis, vernal conjunctivitis, etc.), cutaneous diseases (e.g., contact dermatitis, atopic dermatitis, urticaria, other kind of eczematoid dermatitis, etc.), inflammatory diseases (e.g., rheumatoid arthritis, osteoarthritis, etc.), pain or aches ( e.g., migraine, headache, toothache, cancerous pain, backpain, etc.), and the like.

DISCLOSURE OF THE INVENTION

The object compound of the present invention may be illustrated as the following general formula (I).

$$R^1-A^1-D-Trp(R^2)-A^2-R^3 \quad (I)$$

[wherein
$R^1$ is hydrogen or amino-protective group
$R^2$ is amino-protective group
$R^3$ is ar(lower)alkoxy or N-(lower)alkyl-N-ar(lower)alkylamino
$A^1$ is single bond or one amino acid residue
$A^2$ is one amino acid residue excepting Phe.]

BEST MODE OF THE INVENTION

The object compound (I) of the present invention may be prepared by the method as illustrated as the following reaction scheme.

Preparation Process 1

$$H-A^2-R^3 \quad (IIa)$$
or its reactive
derivative at the
amino group, or the
salt thereof
$$\downarrow R^{1a}-D-Trp(R^2)-OH \quad (IIb)$$
$$\quad \text{or its reactive derivative}$$
$$\quad \text{at the carboxy group, or the}$$
$$\quad \text{salt thereof}$$
$$R^{1a}-D-Trp(R^2)-A^2-R^3 \quad (Ia)$$
or the salt thereof Preparation Process 2

$$R^{1a}-D-Trp(R^2)-A^2-R^3 \quad (Ia)$$
or the salt thereof
$$\downarrow \text{elimination reaction of}$$
$$\quad \text{amino-protective group}$$
$$H-D-Trp(R^2)-A^2-R^3 \quad (Ib)$$
or the salt thereof Preparation Process 3

$$H-D-Trp(R^2)-A^2-R^3 \quad (Ib)$$
or its reactive derivative at the
amino group, or the salt thereof
$$\downarrow R^{1b}-A^1-OH \quad (IIc)$$
$$\quad \text{or its reactive derivative at the}$$
$$\quad \text{carboxy group, or the salt thereof}$$
$$R^{1b}-A^1-D-Trp(R^2)-A^2-R^3 \quad (Ic)$$
or the salt thereof Preparation Process 4

$$R^{1b}-A^1-D-Trp(R^2)-A^2-R^3 \quad (Id)$$
or the salt thereof
$$\downarrow \text{elimination reaction of}$$
$$\quad \text{amino-protective group}$$
$$H-A^1-D-Trp(R^2)-A^2-R^3 \quad (Ie)$$
or the salt thereof Preparation Process 5

$$H-A^1-D-Trp(R^2)-A^2-R^3 \quad (Ie)$$
or its reactive derivative at the
amino group, or the salt thereof
$$\downarrow \text{introduction reaction of}$$
$$\quad \text{amino-protective group}$$
$$R^{1c}-A^1-D-Trp(R^2)-A^2-R^3 \quad (If)$$
or the salt thereof

[In the above reaction scheme, $R^{1a}$, $R^{1b}$, $R^{1c}$ are amino-protective group, $R^1$, $R^2$, $R^3$, $A^1$, $A^2$ are each as defined above]

All the compounds (Ia), (Ib), (It), (Id), (Ie) and (If) illustrated on the above reaction scheme are included in the object compound (I) of the present invention. Accordingly, in the following explanation, these compounds (Ia)–(If) may be generally described as the object compound (I). All the compounds (IIa), (IIb) and (IIc) are used as the starting compound, and some of them are new and may be prepared according to the preparative examples described below or commonly used method.

In the present specification, amino acid, peptide, protective group, condensing agent may be illustrated by showing the abbreviation thereof that are defined at IUPAC-IUB.

In the case that amino acid or its residue is shown by using the above mentioned abbreviation without any specific instruction, it means compounds of L-form and D-form, compound and residue of D-form are shown with an indication of D-.

The suitable salt of the object compound (I) is a conventionally used non-toxic salt that include acid addition salt such as organic acid salt (e.g., acetic acid salt, trifuluoroacetic acid salt, maleic acid salt, tartaric acid salt, methanesulfonic acid salt, benzenesulfonic acid salt, formic acid salt, toluenesulfonic acid salt, etc.), inorganic acid salt (e.g., hydrochloric acid salt, hydrobromic acid salt, hydriodic acid salt, sulfuric acid salt, nitric acid salt, phosphoric acid salt, etc.), salt with amino acid (e.g., arginine, aspargic acid, gulutamic acid, etc.); metal salt such as alkali metal salt (e.g., sodium salt, pottasium salt, etc.,), alkaline earth metal salt (e.g., calcium salt, magnesium salt, etc.); ammonium salt; salt with organic base (e.g., trimethylamine, triethylamine, pyridine, picoline, dicyclohexylamine, N,N'-dibenzylethylenediamine, etc.); and the like.

Several definition used in the afore or below description of the present specification, suitable example and explanation that is included in the scope of the present invention is described as folows.

"Lower" means $C_1$–$C_6$, preferably $_1$–$C_4$.

"Amino acid" in "amino acid residue" which is used for $A^1$ means aliphatic cahain hydrocarbon compound, alcyclic hydrocarbon compound, aromatic hydrocarbon compound, heterocyclic compound, partially hydrogenated compound thereof or dehydroganated compound thereof that is substituted with at least one amino group and at least one carboxy group, and these compounds may be further substituted with any other optical substituent(s).

Specifically suitable amino acid residue means bivalent residue of the above explained amino acid. The suitable example of thus explained amino acid include neutral amino acid such as glycine (gly), D-alanine or L-alanine (Ala), β-alanine (β-Ala), D- or L-valine (Val), D- or L- leucine (Leu), D- or L-isoleucine (Ile), D- or L-serine (Set), D- or L-threonine (Thr), D- or L-cysteine (Cys), D- or L-methyonine (Met), D- or L-phenylalanine (Phe), D- or L-tryptophan (Trp), D- or L-tyrosine (Tyr), D- or L-proline (Pro), D- or L-4-hydroxyproline (Hyp), D- or L-pyroglutaminic acid (pGlu) or the like; acidic amino acid such as D- or L-glutamic acid (Glu), D- or L-aspartic acid (Asp), D- or L-β-aspartic acid (β-Asp), D- or L-glutamic acid (Gln), D- or L-aspargine (Ash) or the like; basic amino acid such as D- or L-lysine (Lys), D- or L-arginine (Arg), D- or L-histidine (His), D- or L-ornithine (Orn), D- or L-pyridylalanine (Pyrala) or the like.

"Amino acid" in "amino acid residue" which is used for $A^2$ means the same amino acid explained for $A^1$ excepting L-Phe (L-phenylalanine). Accordingly, $A^2$ includes D-phenylaianine and substituted L-phenylalanine. Suitable examples of amino acid for $A^2$ include not only any exemplified amino acid for $A^1$ but also N-methylphenylalanine, p-aminobenzoic acid, o-aminobenzoic acid, 1-euninonaphthaline-2-carboxylic acid, 2,3-dihydroindene-2-amino-2-carboxylic acid, pyrole-2-carboxylic acid, 3-pyridylalanine, 3H-indole-2-carboxylic acid, quinoline-2-carboxylic acid, 1,2,3,4-tetrahydroisoquinoline-3-carboxylic acid or the like.

Suitable examples of the group which may be substituted for the above exemplified amino acid include lower alkyl, lower alkoxy, nitro, hydroxy, halogen, aryl, ar(lower)alkyl, heterocyclic group, heterocyclic(lower)alkyl and the like. Any other groups such as the protective group conventionally used in the chemical field of amino acid and peptide may also be exemplified as substituent.

Suitable examples of lower alkyl include methyl, ethyl, propyl, butyl, tert-butyl, hexyl or the like. Suitable examples of lower alkoxy include methoxy, ethoxy, propoxy, butoxy or the like. Halogen includes flurine, chlorine, bromine and iodine. Suitable examples of aryl include phenyl, naphtyl or the like. Suitable examples of ar(lower)alkyl include benzyl, phenetyl or the like. Suitable examples of heterocyclic group include furyl, oxazolyl, oxazolinyl, oxazolidikyl, thienyl, thiazolyl, thiazolinyl, pyrrolyl, pyrrolinyl, pyrrolidyl, pyridyl, pyranyl, quinolyl, isoquinolyl or the like. Suitable examples of heterocyclic(lower)alkyl include 2-(furan-2-yl)ethyl, 2-(oxazoline-3-yl)ethyl, 2-(thiophene-2-yl)ethyl, 3-(thiazoline-3-yl)propyl, 3-(pyrrol-2-yl)propyl, 2-(imidazoline-2-yl)propyl or the like.

More suitable amino acid is α-amino acid of which side chain is substituted with aromatic group residue or heterocyclic group residue, and most suitable examples of amino acid include alanine wherein carbon chain thereof is substituted with aromatic group residue or heterocyclic group residue at 3rd position (e.g., N-methylphenylalanine, D-phenylalanine, tyrosine, 3-thienylalanine, 3-pyridylalanine, tetrahydroisoquinoline-3-carboxylic acid, 2,3-dihydroindene-2-amino-2-carboxylic acid The group "—Trp($R^2$)—" means that $R^2$ is substituted at 1st position of indole ring of tryptophan residue.

Suitable examples of amino-protective group include the conventional protective one that is usually applied in the chemical field of amino acid or peptide, for example ar(lower)alkyl such as trityl, benzhydryl, benzyl, etc., dinitrophenyl, lower alkoxycarbonyl(lower)alkenyl such as 1-methoxycarbonyl-1-propene-1-yl, etc., aroyl(lower)alkenyl such as 1-benzoyl-1-propene-2-yl, hydroxyar(lower)alkylidene such as 2-hydroxybenzilidene, etc., silyl compound such as tri(lower)alkylsilyl (e.g., trimethylsilyl etc.), etc., and the acyl group as shown as follows.

Suitable acyl groups include aliphatic acyl, aromatic acyl, heterocyclic acyl, andaliphatic acyl that are substituted with aromatic residue or heterocyclic residue, and the like.

Suitable examples of aliphatic acyl include saturated or unsaturated, acyclic or cyclic acyl for example, cabamoyl, lower alkanoyl (e.g., formyl, acetyl, propionyl, butyryl, isobutyryl, varelyl, isovarelyl, pivaroyl, hexanoyl, etc.), lower alkane sulfonyl (e.g., mesyl, ethanesulfonyl, propanesulfonyl, etc.), lower alkoxycarbonyl (e.g., methoxycarbonyl, ethoxycarbonyl, propoxycarbonyl, butoxycarbonyl, tert-butoxycarbonyl, etc.), lower alkenoyl (e.g., acryloyl, methacryloyl, crotonoyl, etc.), ($C_3$–$C_7$)cycloalkanecarbonyl (e.g., cyclohexane carbonyl, etc.), amidino, protected carboxycarbonyl such as lower alkoxalyl (e.g., methoxalyl, ethoxalyl, tert-butoxalyl, etc.), and the like.

Suitable examples of aromatic acyl include aroyl (e.g., benzoyl, toluoyl, xuloyl, etc.), arenesulfonyl (e.g., benzenesulfonyl, tosyl, etc.), and the like.

Suitable examples of heterocyclic acyl include heterocyclic carbonyl (e.g., furoyl, thenoyl, nicotinoyl, isonicotinoyl, thiazolylcarbonyl, thiadiazolylcarbonyl, tetrazolylcarbonyl, morpholinocarbonyl, etc.) and the like.

Suitable examples of aliphatic acyl substituted with aromatic group include ar(lower)alkanoyl such as phenyl(lower)alkanoyl [e.g., phenylacetyl, phenylpropionyl, phenylhexanoyl, etc.], at(lower)alkoxycarbonyl such as phenyl(lower)alkoxycarbonyl [e.g., benzyloxycarbonyl, phenetyloxycarbonyl, etc.] and the like.

Suitable examples of aliphatic acyl substituted with heterocyclic group include thienylacetyl, imidazolylacetyl, furylacetyl, terazolylacetyl, thiazolylacetyl, thiadiazolylacetyl, thienylpropyl, thiadiazolylpropionyl, and the like.

These acyl group may be further illustrated such as carboxy, lower alkyl [e.g., methyl ethyl, propyl, isopropyl, butyl, tert-butyl, pentyl, hexyl, etc.], halogen [i.e., chlorine, bromine, iodine, fluorine], carbamoyl, lower alkanoyl [e.g., formyl, acetyl, propionyl, etc.], ar(lower)alkanoyl [e.g., benzyl, etc.], lower alkyl [e.g., methyl ethyl, propyl, isopropyl, butyl, tert-butyl, pentyl, hexyl, etc.], lower alkoxycarbonyl [e.g., methoxycarbonyl, ethoxycarbonyl, tert-butoxycarbonyl, etc.], carboxy(lower)alkyl [e.g., carboxymethyl, carboxyethyl, etc.], protected carboxy(lower)alkyl [e.g., tert-butoxycarbonylmethyl, etc.] and the like.

Suitable examples of ar(lower)alkoxy of $R^3$ include benzyloxy, phenetyloxy, trityloxy, 3-phenyl-propoxy, 4-phenylbutoxy, benzhydryloxy and the like.

Suitable examples of N-(lower)alkyl-N-ar(lower)alkylamino of $R^3$ include N-methyl-N-benzylamino, N-methyl-N-phenetylamino, N-methyl-N-tritylamino, N-methyl-N-benzhydrylamino, N-ethyl-N-benzylamino, N-ethyl-N-phenetylamino and the like.

Suitable examples of each group of $R^1$, $R^2$, $R^3$, $A^1$ and $A^2$ are explained as follows.

$R^1$ is hydrogen; acyl; carbamoyl; lower alkoxycarbonyl such as methoxycarbamoyl, ethoxycarbaraoyl, tert-butoxycarbamoyl, etc.; lower alkanoyl such as formyl, acetyl, propionyl, butylyl, etc.; ar(lower)alkoxycarbonyl such as mono- di- or tri-phenyl(lower)alkoxycarbonyl [e.g., benzyloxycarbonyl, etc.]; carbamoyl(lower)alkanoyl such as carbamoylacetyl, succinamoyl, etc.; lower alkoxalyl such as methoxalyl, tert-butoxalyl, etc.; di(lower)alkylamino(lower)alkanoyl such as dimethylaminoacetyl, diethylaminoacetyl, diethylaminopropionyl etc.; N-ar(lower)alkyl-N-lower-alkoxycarbonylamino(lower)alkanoyl such as N-mono-, di- or tri-phenyl(lower)alkyl-N-lower-alkoxycarbonylamino(lower)alkanoyl e.g., N-benzyl-N-tert-butoxycarbonylaminoacetyl etc.]; heterocyclic(lower)alkanoyl optionally substituted with acylamino such as tetrazolyl(lower)alkanoyl [e.g., tetrazolylacetyl, etc.], acylaminothiazolyl(lower)alkanoyl which may have acylamino on alkanoyl such as lower alkanoylamino-thiazolyl(lower)alkanoyl [e.g., formamidothiazolylacetyl, etc.], thiazolyl(lower)alkanoyl having lower alkoxycarbonylamino or lower alkanoylamino on alkanoyl such as 2-formamidolacetyl, -2-tert-butoxycarbonylthiazolylacetyl, 2-formamidothiazolyl-2-acetoamidoacetyl, etc.; carboxy(lower)alkanoyl such as oxalo, carboxyacetyl, carboxypropionyl, carboxybutylyl, carboxyvarelyl, etc,; hydroxy(lower)alkanoyl such as hydroxyacetyl, etc.; heterocyclic carbonyl such as morpholinecarbonyl [e.g., 4-morpholinecarbonyl, etc.], etc.; lower alkylcarbamoyl such as methylcarbamoyl, tert-butylcarbamoyl, etc.; carboxy(lower)alkylamino(lower)alkanoyl such as carboxymethylaminoacetyl, etc.; ar(lower)alkylamino(lower)alkanoyl such di- or tri-phenyl(lower)alkylamino(lower)alkanoyl [e.g., benzylaminoacetyl, etc.], etc.; N-loweralkoxycarbonyl-N-loweralkoxycarbonyl(lower)-alkylamino(lower)alkanoyl such as N-tert-butoxycarbonyl-N-tert-butoxycarbonylmethylaminoacetyl.

$R^2$ is acyl [e.g., lower alkanoyl (e.g., formyl, acetyl, etc.), arenesulfonyl (e.g., benzenesulfonyl, toluenesulfonyl, etc.),etc.]; carbamoyl(lower)alkyl (e.g., carbamoylmethyl, etc.); esterified carboxy(lower)alkyl [e.g., lower alkoxycarbonyl(lower)alkyl (e.g., ethoxycarbonylmethyl, etc.), etc.]; carboxy(lower)alkyl [e.g., carboxymethyl, etc.] and the like.

$R^3$ is ar(lower)alkoxy [e.g., mono-, di- or tri-phenyl ( lower ) alkoxy (e.g., benzyloxy, phenethyloxy, etc. ), etc.]; N-(lower)alkyl-N-ar(lower)alkylamino [e.g., N-methyl-N-benzylamino, N-ethyl-N-benzylamino, etc.] and the like.

$A^1$ is glutamine, serine, asparagine, glutamic acid, threonine, lysine, histidine, β-aspargic acid, ornitine, glycine, tyrosine, triptophane, hydroxypurine, pyroglutamic acid, β-alanine, $N^5,N^5$-di(lower)alkylglutamine, $N^6$-trihalo(lower)alkoxycarbonyllysine, $N^6$-ar(lower)alkoxycarbonyllysine, $N^{-\tau}$ arenesulfonylhistidine, $N^6$-ar(lower)alkoxycarbonylornitine, $N^6$-haloar(lower)alkoxycarbonyllisine, $O^3$-ar(lower)alkylthreonine, N-loweralkylthreonine, glutamic acid $O^5$-trihalo(lower)alkyl ester, $O^3$-carboxy(lower)alkanoylthreonine, and the like.

$A^2$ is glysine, phenylglysine, tirosine, lysine, D-phenylalnine, methylphenylalanine, 3-pyridylalanine, 3-thienylalanine, 1,2,3,4-tetrahydroisoquinoline-3-carboxylic acid, 2,3-dihydroindene-2-amino-2-carboxylic acid, and the like.

The method for preparation of the object compound (I) is described as follows.

Preparation 1

The object compound (Ia) or the salt thereof may be prepared by reacting the compound (IIa) or the reactive derivative at the amino group or the salt thereof with the compound (IIb) or the reactive derivative at the carboxy group or the salt thereof.

Suitable examples of the reactive derivative at amino group of the compound (IIa) include shiff base type imino or enamine type tautomerism thereof formed by the reaction between the compound (IIa) and carbonyl compound such as aldehyde or ketone; silyl derivative formed by the reaction between the compound (IIa) and silyl compound such as bis(trimethylsilyl)acetamide, mono(trimethylsilyl)acetamide, bis(trimethylsilyl)urea, etc.; the derivative formed by the reaction between the compound (IIa) and phosphorous trichloride or phosgene.; and the like.

Suitable example of the salt of the compound (IIa) or the reactive derivative thereof should be reffered to one exemplified for that of the compound (I).

As suitable reactive derivative at carboxy group of the compound (IIa), acid halide, acid anhydride, activated aido, activated ester are exmplified. Suitable examples of the reactive derivative include acid halide; acid azide; mixed acid anhydride such as an anhydride with substituted phosphoric acid (e.g., dialkyl phosphoric acid, phenyl phosphoric acid, diphenylphosphoic acid, dibenzylphosphoric acid, halogenated phosphoric acid, etc.), dialkyl phosphorous acid, sulfurous acid, thiosulfuric acid, sulfuric acid, sulfonic acid (e.g., methanesulfonic acid, etc.), aliphatic carboxylic acid (e.g., acetic acid, propionic acid, burytic acid, isobutyric acid, pivalic acid, pentanoic acid, isopentanoic acid, 2-ethylbutyric acid, trichloroacetic acid, etc.), aromatic carboxylic acid (e.g., benzoic acid, etc.) or the like; symmetric acid anhydride; activated amide with amine such as imidazole, 4-substituted imidazole, dimethylpyrrazole, triazole, tetrazole, or the like; activated ester such as cyanomethyl ester, dimethyliminomethyl[$(CH_3)_2N=CH-$]ester, 2,4-dinitrophenyl ester, trichlorophenyl ester, pentachlorophenyl ester, mesylphenyl ester, phenylazophenyl ester, phenylthio ester, p-nitrophenylthio ester, p-crezylthio ester, carboxymethylthio ester, pyranyl ester, pyridyl ester, piperikyl ester, 8-quinolylthio ester, or the like; ester with N-hydroxy compound (e.g., N,N-dimethylhydroxylamine, 1-hydroxy-2-(1H)-pyridone, N-hydroxysuccinimide, N-hydroxyphthalimide, 1-hydroxy-1H-benzotriazole, or the like. Thus exemplified reactive derivatives may be selected according to the kind of the compound (IIb).

Suitable examples of salt of the compound (IIb) or the reactive dericvative thereof include salt with base such as alkali metal salt (e.g., sodium salt, potassium salt, etc.), alkaline earth metal salt (e.g., calcium salt, magnesium salt, etc.), ammonium salt, salt with organic base (e.g., trimethylamine, triethylamine, pyridine, picoline, dicyclohexylamine, N,N'-dibenzylethylenediamine, etc.), or acid addition salt as exemplified as the salt of the compound (I).

The present reaction is usually carried out in a conventional solvent such as water, alcohol (e.g., methanol, ethanol, etc.), acetone, dioxane, acetonirile, chloroform, methylene chloride, ethylene chloride, tetrahydrofuran, ethyl acetate, N,N-dimethylformamide, pyridine, or any other organic solvent which does not adversely affect the proceeding of the reaction. These solvent may be used as a mixture with water.

In the case that the compound (IIb) is used as free acid or the salt thereof, may be used conventional condensing agent such N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; phosphorous acid trialkyl ester; poly ethyl phosphate, poly isopropyl phosphate; phosphoryl chloride; phosphorous trichloride; diphenylphospholyl azide; thionyl chloride; oxalyl chloride; lower alkyl haloformate [e.g., ethyl chloroformate, isopropyl chloroformate, etc.]; triphenylphosphine; 2-ethyl-7-hydroxybenzisoxazolium salt; 2-ethyl-5-(m-sulfophenyl isoxazolium hydroxide iner salt; 1-(p-chlorobenzenesulfonyloxy)-6-chloro-1H-benzotriazole; Viles-Meyer reagent prepared by reacting N,N-dimethylformamide with thionyl chlride, phosgene, trichlomethyl chloroformate, phosphorous oxychloride, etc..

The reaction may be also carried out in the presence of inorganic or organic base such as alkali metal bicarbonate, tri(lower)alkylamine, pyridine, N-(lower)alkylmorpholine, N,N-di(lower)alkylbenzylamine or the like.

The reaction is usually carried out under cooling or warming though the reaction tempertature is not limited.

Preparation 2

The object compound (Ib) or the salt thereof may be prepared by subjecting the compound (Ia) or the salt thereof to eliminating reaction of amino-protective group.

Suitable example of the salt of the compound (Ia) and (Ib) should be reffered to the exemplified salts of the compound (I).

The present reaction is carried out according to the conventional hydrolysis or reduction.

The hydrolysis is preferably carried out in the presence of base or acid including Lewis-acid.

Suitable examples of the base include inorganic base and organic base such as alkali metal (e.g., sodium, potassium, etc), alkaline earth metal (e.g., magnesium, calcium, etc.), metal hydroxide, carbonate or bicarbonate thefor, trialkylamine (e.g., trimethylamine, triethylamine, etc.), picoline, 1,5-diazabicyclo[4.3.0]none-5-ene, 1,4-diazabicyclo[2.2.2]octane, 1,8-diazabicyclo[5-4.0]undes-7-ene and the like.

Suitable examples of the acid include organic acid such as formic acid, acetic acid, propionic acid, trichloroacetic acid, trifluoroacetic acid, etc., inorgannic acid such as hydrochloric acid, hydrobromic acid, sulfuric acid, hydrochloride, hydrobromide, hydrofluoride, etc. or acid addition salt such as hydrochlolic acid salt of pyridine etc..

The elimination reaction which is used Lewis-acid such as trihaloacetic acid (e.g., trichlroacetic acid, trifluoroacetic acid, etc.) is preferably carried out in the presence of cation catching agent such as anisole, phenol, or the like.

The present reaction is usually carried out in a conventional solvent such as water, alcohol (e.g., methanol, ethanol, etc.), methylene chloride, chloroform, tetrachloromethane, tetrahydrofanan, the mixture thereof or any other organic solvent which does not adversely affect the proceeding of of the reaction. Liquid base and acid may also be used as solvent.

The reaction tempertature is not limited, and therefore the reaction is usually carried out under cooling or heating.

Reduction reaction which is applied for the elimination reaction includes chemical reduction and contact reduction.

Suitable examples of the reducing agent which is used for chemical reduction include metal (e.g., tin, zinc, iron, etc.), or the combination of metal compound (e.g., chromic chloride, chromic acetate, etc.) and organic or inorganic acid (e.g., formic acid, acetic acid, propionic acid, p-toluenesulfonic acid, hydrochloric acid, hydrobromic acid, etc.).

Suitable examples of the catalyst which is used for contact reduction include conventional catalyst such as palldium catalyst (e.g., platinum board, platinum sponge, platinum black, colloidal platinum, platinum oxide, platinum wire, etc.), palladium catalyst (e.g., palladium sponge, palladium-black, palladium oxide, palladium-carbon, colloidal palladium, palladium-barium carbo-nate, palladium-barium sulfonate, etc.), nickel catalyst (e.g., reduced nickel, oxidized nickel, Raney-nickel, etc.), cobalt catalyst (e.g., reduced cobalt, Raney-cobalt, etc.), iron catalyst (e.g., reduced iron, Raney-iron, etc.), cupper catalyst (e.g., reduced cupper, Raney-cupper, Ullman-cupper, etc.), and the like.

The reaction is usually carried out in ath conventional solvent which does not adversly affect the proceeding of the reaction such as water, methanol, ethanol, propanol, N,N-dimethylformamide, or the mixture thereof.

Liqiiodous acid which is used for the chemical reduction may also used as a solvent for the reaction. Suitable examples of solvent for contact reduction include conventional one such as diethyl ether, dioxane, tetrahydrofurane and any other solvent illustrated before and a mixture thereof which does not adversely affect the proceeding of the reaction.

The reaction temperature is not limited, and therefore the reaction is usually carried out under cooling or heating.

Preparation 3

The object cmpound (Ic) or the salt thereof may be prepared by reacting the compound (Ib) or the reactive derivative at the amino group or the salt thereof with the compound (IIc) or the reactive derivative at the carboxy group or the salt thereof.

The suitable salt of the compound (Ib) or the reactive derivative therof should be reffered to that illustrated for the compound (IIa).

The suitable salt of the compound (IIc) or the reactive derivative therof should be reffered to that illustrated for the compound (IIb).

The suitable salt of the compound (Ic) should be reffered to that illustrated for the compound (I).

The present reaction is carried out in substantially same manner to that of Preparation 1, and accordingly, the reaction system and the reaction condition such as the kind of the reactive derivative, kind of solvent, reaction temperature should be reffered to that of Preparation 1.

Preparation 4

The object compound (Ie) or the salt thereof may be prepared by subjecting the compound (Id) or the salt thereof to eliminating reaction of amino-protective group.

The present reaction is carried out in substantially same manner to that of Preparation 2, and accordingly, the reaction system and the reaction condition such as the kind of base, acid, reducing agent, catalyst, solvent, temperature, etc. should be reffered to that of Preparation 2.

In the present eliminating reaction the amino-protective group of $R^{1b}$ and/or lower alkyl of $R^3$ may be eliminated during the course of reaction proceeding or after-treatment, which case is included in the scope of the present invention.

Preparation 5

The object compound (If) or the salt thereof may be prepared by subjecting the compound (Ie) or the reactive derivative at amino group or the salt thereof to introducing reaction of amino-protective group.

The present reaction is carried out in substantially same manner to that of Preparation 1, and accordingly, the reaction system and the reaction condition such as the kind of the reactive derivative, kind of solvent, reaction temperature should be reffered to that of Preparation 1.

The compound thus obtained through the above mentioned preparation may be separated and purified by conventional method such as pulverization, recrystallization, calumn chlomatography, repreciptation, or the like.

The compound (I) and any other compound of the present invention may include one more than two steroisomer due to asymmetric carbon atom, and these isomer or the mixture thereof is included in the scope of the present invention.

The object compound (I) and the salt thereof has a pharmaceutical activity such as tachykinin antagonism, especially substance P compound antagonism, neurochinin A antagonism, neurochinin B antagonism, and the like. Accordingly it is useful for therapeuticts or prevention of tachykinin mediated diseases such as respiratory diseases (e.g., asthma, bronchitis, rhiniris, cough, expectoration, etc.), ophthalmic diseases (e.g., conjunctivitis, vernal conjunctivitis, etc-), cutaneous diseases (e.g., contact dermatitis, atopic dermatitis, urticaria, other kind of eczematoid dermatitis, etc.), inflammatory diseases (e.g., rheumatoid arthritis, esteoarthritis, etc.), pains or aches (e.g., migraine, headache, toothache, cancerous pain, backpain, etc.), and the like.

Further the object compound (I) of the present invention are also useful for treating or preventing of other kind of diseases such as ophthalmic diseases (e.g., glaucoma, uveitis, etc.); gastrointestinal disseases (e.g., ulcer, ulcerafire coliris, irritable bowel syndrome, food allergy, etc.); inflammatory diseases (e.g., nephritis, etc.); circulatory diseases (e.g., hypertension, angina pectoris, cartiac failure, thrombosis, etc.,); epilepsy; spastic paralysis; pollakiuria; dementia; Alzheimer's disease; schizophrenia; Hungtinton chorea; carcinoid syndrome, and the like.

The object compound (I) or the salt thereof is used in the form of a pharmaceutical preparation, which contains the above compound as an active ingredient in admixture with an organic or inorganic, solid or liquid carrier that is pharmaceutically acceptable and is suitable for peroral, patenfetal or external application. The pharmaceutical composition may be prepared as capsule, tablet, sugar coated tablet, granule, solution, suspension, emulsion, or any other form suitable for use, which may include, if neccesary, conventional additives such as auxiliary agent, stabilizing agent, wetting agent, emulsifying agent, Doffers, or the like.

The dosage of therapeutically or preventively effective amount of the object compound (I) varies from and also depend upon the age and condition of each individual patient to be treated. An average single dose, for example in effective treatment of asthma, of about 0.1 mg, 1 mg, 50 mg, 100 mg, 250 mg and 1,000 mg is generally administered.

As examples for showing such pharmacological effect of the object compound (I), the pharmacological test data of the representaive compound is illustrated as follows.

TEST METHOD

1. Binding with $^3$H-P substance receptor
(a) Crude lung membrane preparation

Male Hartly strain guinea pigs were sacrificed by decapitation, The trachea and lung were removed and homogenized in buffer (0.25M sucrose, 50 mM Tris-HCl pH 7.5, 0.1 mM MEDTA) by using Polytoron (Kinematica). The homogenate was centrifuged (1000 x g, 10 min) to remove tissue clumps and the supernatant was centrifuges (14000 x g, 20 min) to yield pellets. The pellets were resuspended in buffer (5 mM Tris-HCl pH 7.5), homofenized with a teflon homogenizer and centrifuged (14000 x g, 20 min) to yield pellets which were referred to crude membrane fractions. The obtained pallets were stored at $-70\,°$ C. until use.

(b) $^3$H-Substance P binding to preparation membrane

Frozen crude membrane fractions were thawed and resuspended in Medium 1 (50 mM Tris-HCl pH 7.5, 5 mM $MnCl_2$, 0.02% BSA, 2 µg/ml chymostatin, 4 µg/ml leupeptin, 40 µg/ml bacitaracin). $^3$H-substance P (1 nM) was incubated with 100 µl of the membrane preparation in Medium 1 at 4° C. for 30 minutes in a final volume of 500 µl. At the end of the incubation over a Whatman GF/B glass filter (pretreated with 0.1% polyethylene imine for 3 hours prior to use) under aspiration. The filters werre then washed four times with 5 ml of the buffer (50 mM Tris-HCl, pH 7.5). The radioactivity was counted in 5 ml of Aquazol-2 in Packerd scintillation counter (Packerd TRI-CARB 4530).

Test Compound

Test compound

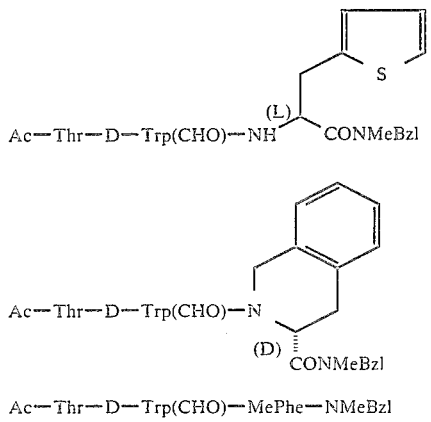

(a) Ac—Thr—D—Trp(CHO)—NH—...—CONMeBzl (b) Ac—Thr—D—Trp(CHO)—N(D)...—CONMeBzl (c) Ac—Thr—D—Trp(CHO)—MePhe—NMeBzl

Result of Test

| test compound (1 µg/ml) | suppression rate (%) |
|---|---|
| (a) | 100 |
| (b) | 99 |
| (c) | 96 |

In the present specification, the following abbreviations are further used in addition to that appointed in IUPAC-IUB.

Ac: acetyl
Ac$_2$O: acetic acid anhydride
Boc: tert-butoxycarbonyl
Bzl: benzyl
DCHA: dicyclohexylimine
DIPEA: diisopropylethylamine
DMF: N,N-dimethylformamide
DMSO: dimethylsulfoxide
Et: ethyl
4N-HCl/DOX: 4N-hydrogenchloride in 1,4-dioxane
HOBT: N-hydroxybenzotriazole
IPE: isopropyl ether
Me: methyl
NMM: N-methylmorpholine
TFA: trifluoroacetic acid
THF: tetrahydrofurann
Tos-Cl: tosylchloride(p-toluenesulfonylchloride)
TsOH: p-toluenesulfonic acid (tosylic acid)
WSC: 1-ethyl-3-(3'-dimethylaminopropyl)-carbodiimide
WSC-HCl: 1-ethyl-3-(3'-dimethylaminopropyl)-carbodiimide hydrochloride Further, in those examples, in the case wherein amino acid residue has the substituent in wherein amino acid residue has the substituent in the side chain, for example,

is illustrated as the formula; —Trp(CHO)—.

Still further, in those examples, the following group;

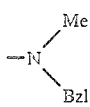

is illustrated as the formula; —NMe(Bzl).

Still further, in those examples, Me-Phe means N-methylphenylalanine.

The present invention is further explained in detail by describing the examples.

EXAMPLE

Preparative Example 1

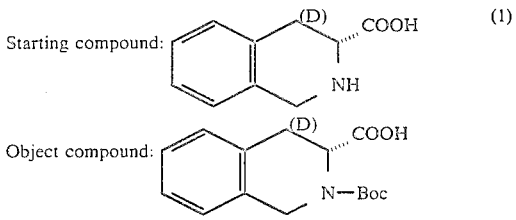

The starting compound (3.30 g) was suspended in water (35 ml), and were added triethylamine (2.22 g) and acetone (10 ml). Acetone solution of (Boc)$_2$O (4.81 g) was added to the above obtained mixture under ice-cooling. The reaction mixture was stirred for 30 minutes at the same temperature, and further for 4 hours after removing off the ice bath. During this stirration, were added dropwise triethylamine (0.44 g) and acetone (15 ml). Acetone was distilled off from the reaction mixture, and then washed with diethyl ether. The aqueous reaction mixture was changed to acidic solution by adding 1N-HCl. After extracting twice with ethyl acetate, the extracts were gathered and washed twice with brine and dried over anthydrous magnesium sulfate. The extract was condensed under reduced pressure and IPE was added to the residue to give the solidified object compound (3.40 g).

NMR(CDCl$_3$, δ): 1.48(9H, s), 3.22(2H, d,J=6 Hz), 4.62(ABq, 4H, J=18 Hz),5.1(1H,m), 7.20(4H,s),7.96(1H,s)

Starting compound: 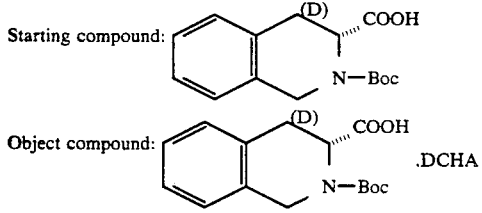 (2)

Object compound: 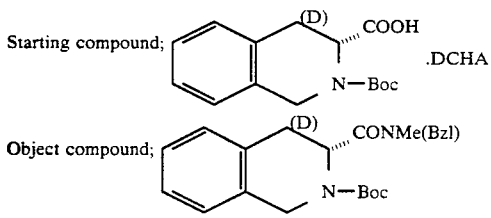 .DCHA

The starting compound (3.30 g) was disolved in a mixed solution of ethyl ether (80 ml) and ethyl acetate (20 ml), and then DCHA(2.05 g) was added under ice-cooling. The reaction mixture was condensed to 20 ml, and was added IPE(15 ml). The resutant solution was kept standing in a cold box for a night. The precipitated crystals were gathered by filtration and dried to give the object compound (2.1 g).

mp: 171°–172° C.
IR (Nujol): 2700–2600, 2350, 1695, 1630 cm$^{-1}$

Starting compound; (3) .DCHA

Object compound;

(1) The starting compound (2.28 g) was added to the mixture of 10% citric acid and ethyl acetate. The organic soluton was washed with brine and dried over magnesium sulfate. The solvent was distilled off under reduced pressure to give free acid of the object compound (1.46 g).

(2) Thus obtained compound in (1) was dissolved in methylene chloride (25 ml), and then were added NMM (502.6 mg) and DMF (4 ml) to give a clear solution. Thus obtaind solution was cooled to $-22° \sim -20°$ C. and was added dropwise methylene chloride (4 ml) solution of isobutyl chloroformate (680 mg). After stirring for 20 minutes at the same temperature, the reaction mixture was further cooled to $-40°$ C. and was added HNMe(Bzl) (605 mg). The reaction mixture was brought back to ambient temperature during stirring for 3.5 hours. After condensation under reduced pressure, extract was carried out by ethyl acetate. The extract was washed respectively with dil. hydrochloric acid, water, dil. aqueous solution of sodium bicarbonate and brine, in turn. After drying over anhydrous magnesium sulfate, the solution was condensed under reduced pressure. The precipitated crystals were washed with n-hexane to give the object compound (463 mg).

mp: 99°–100° C.
IR (nujol) 1690, 1660 cm$^{-1}$
NMR(CDCl$_3$, δ):1.45(9H, s),3.07(5H, broad) 4.4–4.9(4H,m), 5.1(1H,m),7.31(9H, s)

Preparation Example 2

Starting compound; 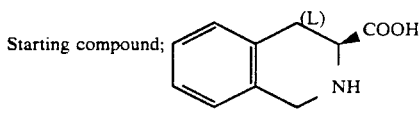

Object compound; 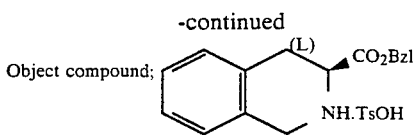

The starting compound (1.5 g), benzylalcohol (4.55 g) and TsOH.H$_2$O (1.76 g) were added to 1,2-dichloroethane (35 ml), and the reaction mixture was refluxed for 10 hours. During this cource, TsOH.H$_2$O (300 mg) was added. The reaction mixture was condensed, and IPE was added to obtain the crystallized object compound (3.76 g).

IR (Nujol): 2650, 2540, 1740, 1225, 1160 cm$^{-1}$
NMR(CDCl$_3$, δ):2.30(3H, s), 3.37(2H, d,J=7 Hz), 4.3–4.7 (3H,m), 5.17(2H, s), 7.01 and 7.50(ABq, 4H, J=8 Hz),7.30(5H, s),6.95–7.4 (4H,m), 9.8(2H,broad)
$[\alpha]_D^{25}$ −39.3°(C=1.046 ,MeOH)

Preparative Example 3

Starting compound; 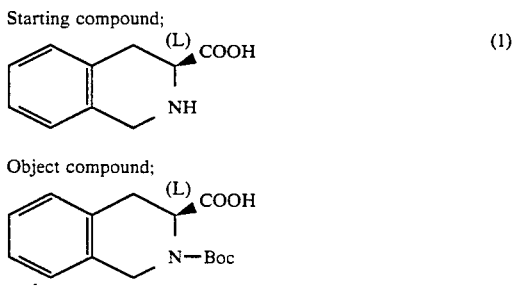 (1)

Object compound;

The object compound was obtained from the starting compound in a similar manner to that of the preparative example 1-(1).

mp: 131°–140° C.
IR ( Nujol): 1710, 1170 cm$^{-1}$ NMR(CDCl$_3$, δ):1.50(9(2H,d,J=7 Hz), 4.58(2H,dd,J=16 Hz), 5.15(1H,m), 7.20(4H, s), 9.62(1H, s)
$[\alpha]_D^{25}$ −9.83° (C=1,MeOH)

Starting compound; 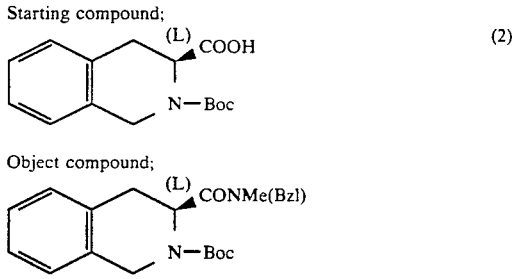 (2)

Object compound;

The starting compound (3.5 g), HNMe(Bzl) (1.53 g) and HOBT(1.71 g) was disolved in DMF (35 ml). After WSC.HCl(2.42 g) was added under ice-cooling, the reaction mixture was stirred at ambient temperature for 6 hours. During this course, WSC.HCl(0.24 g) was added. After concentration, the reaction mixture was extracted with ethyl acetate, and then washed with respctively 2% hydrochloric acid, water, 2% aqueous solution of sodium bicarbonate, water and brine, in order.

After drying by anhydrous mabnesium sulfate, it was condensed under reduced pressure. The residue was developed for column chromatography of silica-gel(200 g), and then was eluted with firstly chloroform and then with a mixed solution of chloroform and methanol (50:1). The fractions containing the object compound were gathered and condensed under reduced pressure. The residue was developed for column chromatography of silica-gel (60 g), and then was eluted with a mixed solvent of ethyl acetate and n-hexane [(⅓)~(1/1)]. The fractions containing the object compound were gathered and the solvent was distilled off under reduced pressure to give the oily object compound (4.04 g).

IR (oil):1690,1660,1165 cm$^{-1}$
NMR(CDCl$_3$, δ):1.1.50(9H, s),3.05(3H, s), 2.85–3.2(2H,m), 4.4–5.1(4H,m),5.3(1H,m),7.2–7.5 (9H,m)
MS: m/e=380

Preparative Example 4 starting compound:

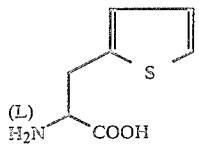
(1)

Object compound:

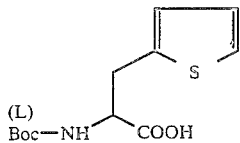

The object compound was obtained from the starting compound in a similar manner to that of the preparative example 1-(1).

NMR(CDCl$_3$, δ):1.25(s) and 1.42(s)(9H) , 3.38(2H, d,J=4 Hz),4.58(m) and 5.20(m)(1H), 6.83-7.28(3H,m), 9.13(1H, s)

Starting compound:
(2)

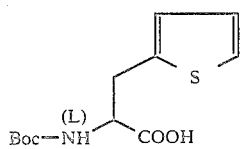

Object compound:

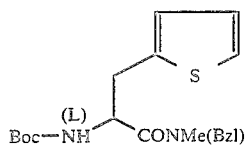

To the solution of methylene chloride ( 25 ml ) of the starting compound (1.59 g), HNMe(Bzl) (679 mg) and HOBT (756 mg) was added WSC.HCl(1.17 g) under ice-cooling. The reaction mixture was stirred for one hour at the same temperature, and further stirred for one night at ambient temperature. After condensation under reduced pressure, the reaction mixture was extracted with ethyl acetate, and then washed respectively with water, dil. aqueous solution of sodium bicarbonate, water, dil. hydrochloric acid and brine in turn. After drying over anhydrous magnesium sulfate, the solution containing the object compound was condensed under reduced pressure. The residue was developed for column chromatography of silica-gel (30 g), and then was eluted with chloroform. The fractions containing the object compound were gathered and the solvent was distilled off under reduced pressure to obtain the object compound (2.2 g).

NMR(CDCl$_3$, δ):1.4(s) and 1.43(s)(9H),2.83(s) and 2.92(s)(3H),3.23(2H,d,J=6 Hz), 4.4–4.6(2H,m), 4.7–5.1(1H,m),5.4(1H,m),6.8–7.4 (8H,m)

Preparative Example 5

Starting compound:

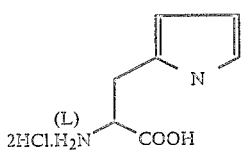

Object compound:

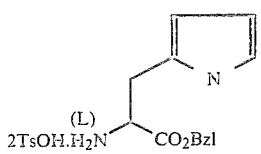

The suspeded solution of benzyl alcohol (20 ml) of the starting compound (3.02 g), TsOH (2.17 g) dried over P$_2$O$_5$ for 5 hours at 100° C. under reduced pressure and Tos-Cl (2.63 g) was refluxed for 3 hours in an oil bath of 90° C., and then heated for one hour under reduced pressure. After ice-cooling, diethyl ether was added to precipitate the gum-like materials, which were gathered by filtration and washed with diethyl ether to obtain the powder of the object compound (7.0 g).

NMR(D$_2$O, δ):2.35(6H, s),3.47–3.77(2H,m), 4.90 and 5.20(2H,ABq, J=12 Hz), 7.0-7.5 (m),7.6-7.8(m) and 8.0–8.3(m)(17H)

Preparative Example 6

Starting compound:

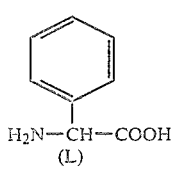

H$_2$N—CH—COOH
(L)

Object compound:

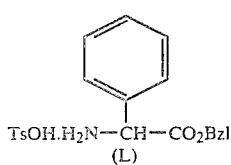

TsOH.H$_2$N—CH—CO$_2$Bzl
(L)

The object compound was obtained from the starting compound in a similar manner to that of the preparative example 2.

mp: 188°–190° C.
IR (Nujol): 2600–2700, 1750, 1740, 1220, 1175 cm$^{-1}$
NMR(DMSO$_6$, δ):2.31(3H,s),5.27(2H,s),5.42(1H,s), 7.32(5H,s),7.5(5H,s),7.13 and 7.53 (4H,ABq,J=8 Hz), 8.93(3H,broad s)

Preparative Example 7

Starting Compound:

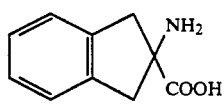

Object compound:

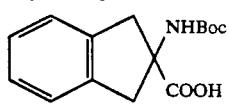

The object compound was obtained from the starting compound in a similar manner to that of the preparative example 1-(1).

mp: 168°-168.5° C. (decomp)
IR (Nujol): 3400, 1760, 1660 cm$^{-1}$
NMR(CDCl$_3$, δ):1.41(9H, s),3.21 and 3.68(4H,ABq,J=16 Hz), 5.3(1H,broad), 7.21(4H, s), 9.43(1H,broad)

Starting compound:

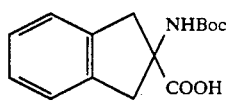

Object compound:

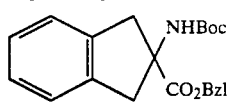

To the solution of DMF (30 ml) of the starting compound (3.32 g) was added DIPEA (2.29 ml) under ice-cooling, and further added benzyl bromide (2.25 g). The reaction mixture was stirred for 1.5 hours at the same temperature and further for 3 hours at ambient temperature. The reaction mixture was condensed under reduced pressure and extracted with ethyl acetate. The extract was washed respectively with water, dil. aqueous solution of sodium bicarbonate, water and brine in turn. After drying over anhydrous magnesium sulfate, the solvent was distilled off under reduced pressure to obtain the object compound (4.23 g).

mp: 107°-108° C.
IR (Nujol): 3400, 1735, 1.710 cm$^{-1}$
NMR(CDCl$_3$ δ):1.38(9H, s), 3.20 and 3.70(4H,ABq, J=18 Hz), 5.22(2H, s),7.20(4H, s),7.32(5H, s)

Starting compound:

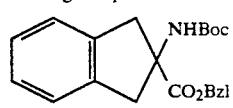

Object compound:

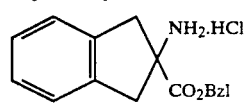

To the mixture of the starting compound (4.2 g) and anisol (4 ml) was added TFA(40 ml) under ice-cooling. The resultant mixture was stirred for 15 minutes at the same temperature and 25 minutes at ambient temperature. After concentration under reduced pressure, 4N-HCl/DOX(5.7 ml) was added thereto and condenced again. IPE was added to the residue to precipitate crystals, which were gathered by filtration to obtain the object compound (3.30 g).

mp: 200 ° C. (decomp)
IR(Nujol): 2760, 2710, 2610, 2590, 2490, 1735, 1605, 1510, 1232 cm$^{-1}$

Preparative Example 8

(1)
Starting compound: Boc-MePhe-OH
Object compound: Boc-MePhe-NMe(Bzl)
The object compound was obtained from the starting compound in a similar manner to that of the preparative example 3-(2).

mp: 74°-75° C.
IR (Nujol): 1680, 1645 cm$^{-1}$
NMR(DMSO-d$_6$, δ):0.94(s),1.12(s) and 1.27(s)(9H), 2.6-3.1(2H,m),2.71(3H, s),2.82(3H, s), 4.2-4.7(2H,m),4-.9-5.4(1H,m),6.9-7.4 (10H,m)

(2)
Starting compound: Boc-MePhe-NMe(Bzl)
Object compound: HCl.H-MePhe-NMe(Bzl)
The object compound was obtained f tom the starting compound in a similar manner to that of the preparative example 7- ( 3 ) .

IR (Nujol): 2700, 2450, 1640 cm$^{-1}$
NMR(DMSO-d$_6$, δ):2.47(3H, s),2.51(3H, s),2.7-3.6(2H,m), 4.40(2H, s),4.64(1H,dd, J=6 Hz and 9 Hz), 6.9-7.4(10H,m),9.5(2H, broad s)

Preparative Example 9

(1)
Starting compound: Boc-MePhe-OH
Object compound: Boc-MePhe-OBzl
The object compound was obtained from the starting compound in a similar manner to that of the preparative example 7-(2).

IR (Film): 1740, 1705, 1690 cm.$^{-1}$
NMR(DMSO-d$_6$, δ): 1.28(9H,s),2.60(3H,s),2.9-3.3(2H,m), 4.6-4.9(1H,m),5.21(2H, s), 7.33(5H, s),7.44(5H, s)

(2)
Starting compound: Boc-MePhe-OBzl
Object compound: HCl-H-MePhe-OBzl
The object compound was obtained from the starting compound in a similar manner to that of the preparative example 7-(3).

IR (Nujol): 2800-2300,1740 cm$^{-1}$
NMR(DMSO-d$_6$, δ):2.59(3H, s),3.12(1H,dd, J=9 Hz and 14 Hz), 3.44(1H,dd, J=5 Hz and 14 Hz),4.36(1H,dd, J=5 Hz and 9 Hz),5.13(2H, s),7.1-7.4(10H,m),10.0(2H,broad s)

Preparative Example 10

Starting compound:
(D.L)

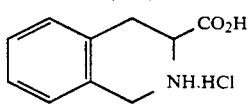

Object compound:

-continued

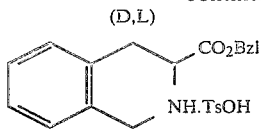

The object compound was obtained from the starting compound in a similar manner to that of the preparative example 2.

mp: 98°–102° C. (decomp)
IR (Nujol):1740, 2750, 2650, 2540, 1225, 1160 cm$^{-1}$
NMR(CDCl$_3$, δ):2.33(3H, s), 3.35(2H, d,J=6 Hz), 4.6(2H,broad), 5.18(2H, s),6.67(1H,broad), 7.03 and 7.57(4H, ABq, J=8 Hz), 7.2(4H,s), 7.35(5H, s),9.73(2H,broad)

EXAMPLE 1

Starting compound:

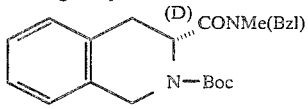

Object compound:

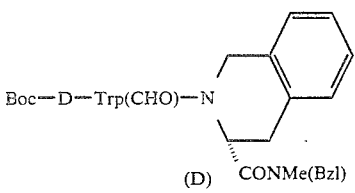

① To the starting compound (695 mg) was added TFA(11 ml) under ice-coiling, and then the reaction mixture was stirred for 15 minutes at the same temperature and further for 20 minutes removing off the ice bath. After condensing under reduced pressure, methylene chloride (30 ml) was added, and dil. aqueous solution of sodium bicarbonate was further added to neutralize the solution. The organic layer was separated by filtration and dried over anhydrous magnesium sulfate.

② To thus obtained dry organic layer were added Boc-D-Trp(CHO)-OH (614 mg), HOBT (257 mg) and WSC-HCl (363 mg). The reaction mixture was stirred for 2 days. During this stir, WSC.HCl(170 mg) was added, and then NMM was added to neutralize the reaction mixture, which was then stirred at ambient tempreture. After the reaction was over, the reaction mixture was washed respectively with water, aqueous solution of sodium bicarbonate, dil. hydrochloric acid and brine in turn, and then dried over anhydrous magnesium sulfate. The solvent was distilled off under reduced pressure to obtain the object compound (1.15 g).

EXAMPLE 2

Starting compound:

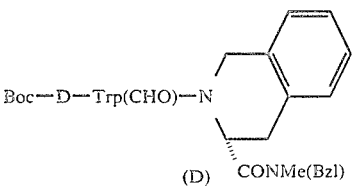

[Intermediate compound:

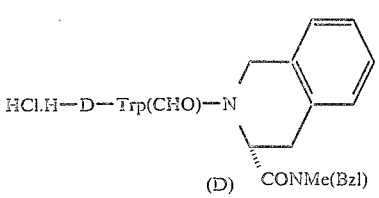

Object compound:

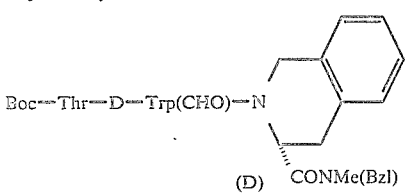

① To the starting compound (1.15 g) was added anisole (1.0 ml), and further added TFA (20 ml) under ice-cooling. The reaction mixture was stirred for 30 minutes. After condensing under reduced pressure, 4N-HCl/DOX (0.9 ml) was added, and further condensed under reduced pressure. IPE was added to obtain the powder of the intermediate compound (1.29 g).

② Thus obtained intermediate compound (1.25 g), Boc-Thr-OH (401 mg) and HOBT (247 mg) were dissolved in methylene chloride (20 ml) , and then WSC(284 mg) was added under ice-cooling. The reaction mixture was stirred for 2 hours. During this course, triethylamine was added to control pH 3. After reaction was over, the reaction mixture was condensed and extracted with ethyl acetate. The extract was washed respectively with water, dil. aqueous solution of sodium bicarbonate, 0.5N-HCl and brine in turn. After drying over anhydrous magnesium sulfate, the extract was condensed under reduced pressure. The residue was developed for column chlomatography of silica-gel (20 g) and, eluted firstly with chloroform and then with a mixture of chloroform-methanol [(100:1)→(100:1.5)]. The fractions containing the object compound was gathered and the solvent was distilled off to obtain the object compound (1.08 g).

NMR (CDCl$_3$: δ):1.12(s) and 1.21(s)(3H,J=7 Hz), 1.37(s) and 1.45(s)(9H),2.8-3.4(7H,m), 3.6(1H,m), 3.9-4.9 (6H,m),5.0-5.6(2H,m),6.6(1H,broad), 6.9-7.8(13H,m),8.3(1H,broad),8.8(1H,broad)

EXAMPLE 3

Starting compound:

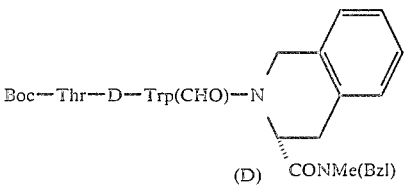

[Intermediate compound:

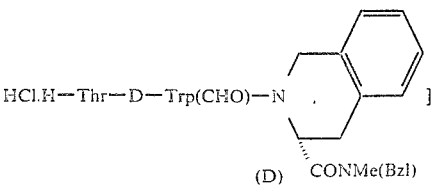

Object compound:

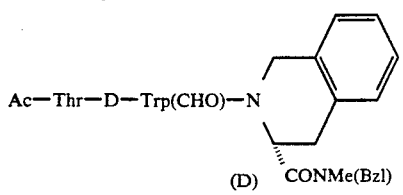

Ac—Thr—D—Trp(CHO)—N (D)  CONMe(Bzl)

① The starting compound (1.05 g) and anisole (1.0 ml) were dissolved in methylene chloride (10 ml), and 4N-HCl/DOX (10 ml) was added thereto under ice-cooling. The reaction mixture was stirred for 20 minutes at the same temperature and then removed off the ice bath to continue stirring for further 30 minutes. The reaction was condensed under reduced pressure. IPE was added to the residue to obtain the powder of the intermediate compound (864 mg).

② Thus obtained intermediate compound (864 mg) was dissolved in dichloromethane (10 ml) under cooling with CCl$_4$—CO$_2$, and triethylamine (276 mg) and AC$_2$O (140 mg) were added thereto. The reaction was carried for 1.5 hour. During this reaction course Ac$_2$O (109 mg) was added thereto. After reaction was over, water was added to the reaction mixture. The organic layer was separated and washed respectively with water, dil. aqueous solution of sodium bicarbonate, dil. hydlochloric acid and brine in turn. After drying over anhydrous magnesium sulfate, the organic solvent was distilled off under reduced pressure. The residue was developed for column chromatography of silica-gel (20 g) and extracted with firstly chloroform, and then with a mixture of chloroform-methanol [(100:1)→(100:3)]. The fractions containing the object compound was gathered and the solvent was distilled off to obtain the object compound (575 mg).

IR (Nujol): 3300, 1710, 1660(sh),1630 cm$^{-1}$

NMR(CDCl$_3$, δ) :1.16(3H,d,J=7 Hz),2.03(3H, s), 2.75-3.34(7H,m),3.4-3.7(1H,m), 4.2-4.8(6H,m), 5.0-5.6(2H,m),6.3-6.6(1H,m),6.9-7.7(13H,m), 8.2 ( 1H, m), 8.82 ( 1H, broad)

EXAMPLE 4

Starting compound:

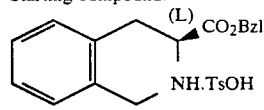

NH.TsOH

Object compound:

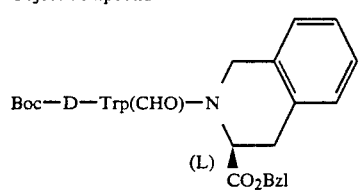

Boc—D—Trp(CHO)—N (L) CO$_2$Bzl

The starting compound (1.32 g), Boc-D-Trp(CHO)-OH (1.0 g) and HOBT (406 mg) were added to the mixed solvent of methylene chloride (20 ml) and DMF(5 ml) , and WSC(513 mg) was added thereto under ice-coiling. The reaction was stirred for 2 hours under at the same temperture. The reaction mixture was kept standing for 3 days at 5° C., and condensed under reduced pressure. The residue was extracted with ethyl acetate, and then was washed respectively with dil. aqueous solution of sodium bicarbonate, dil. hydrochloric acid and brine in turn. After drying over anhydrous magnesium sulfate, the solvent was distilled off under reduced pressure to obtain the object compound (1.76 g).

NMR(CDCl$_3$, δ):1.45(s) and 1.50(s)(9H),2.8-3.4(4H,m), 4.1-4.9(2H,m),5-.2-5.7(2H,m), 6.5(1H,m), 7.0-7.7(9H,m),8.2(1H,m),8.9(1H,m)

EXAMPLE 5

Starting compound:

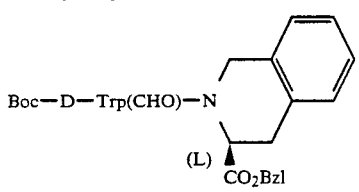

Boc—D—Trp(CHO)—N (L) CO$_2$Bzl

Object compound:

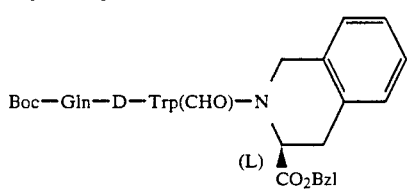

Boc—Gln—D—Trp(CHO)—N (L) CO$_2$Bzl

The object compound was obtained from the starting compound in a similar manner to that of example 2 by using Boc-Gln-OH in stead of e Boc-Thr-OH.

mp: ~82° C.

IR (Nujol): 3300, 1710, 1660, 1170 cm$^{-1}$

NMR(CDCl$_3$, δ):1.35(s) and 1.43(s)(9H),1.9-2.4 (4H,m), 3.0-3.3(4H,m),4.3(3H,m),4.86(s) and 5.02(s)(2H),5.2-5.5(2H,m),5.8(1H,m),6.3(1H,m), 6.9-7.4 (14H,m),7.6(2H,m),8.1(1H,m),8.92(1H, s)

Chemical analysis as C$_{39}$H$_{43}$N$_5$O$_6$.2H$_2$O

| | |
|---|---|
| Calcuration | C 62.86, H 6.35, N 9.38 |
| Found | C 62.49, H 5.73, N 9.11 |

EXAMPLE 6

Starting compound:

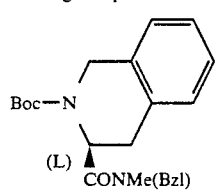

Boc—N (L) CONMe(Bzl)

Object compound:

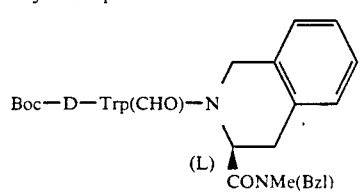

Boc—D—Trp(CHO)—N (L) CONMe(Bzl)

To the solution of methylene chloride (5 ml) of the starting compound (1.38 g) and anisole (2 ml) was added TFA(12 ml) under ice-cooling. The reaction mixture was stirred for 15 minutes at the same temperature and further 1.15 hour at ambient temperature. After condensation under reduced pressure, 4N-HCl/DOX (1.8 ml) was added thereto, and the resultant mixture was condensed again. The residue was dissolved in methylene chloride and washed with dil. aqueous solution of sodium bicarbonate, and then dried over anhydrous magnesium sulfate. Then, DMF, BOC-D-Trp(CHO)-OH (603 mg) and HOBT(246 mg) were added thereto. To the resultant mixture was added WSC.HCl(350 mg) under ice-cooling. The mixture was kept standing for several hours to return ambient temperature and stirred for one night at the same temperature. During this course, Boc-D-Trp(CHO)-OH (603 mg) and WSC.HCl (350 ml) was added thereto. After condensation under reduced pressure, the residue was extracted with ethyl acetate. The extract was washed respectively with water, dil. aqueous solution of sodium bicarbonate, dil. hydrochloric acid and brine in turn. After drying over anhydrous magnesium sulfate, the residue was developed for column chromatography of silica-gel (40 g) and eluted with chloroform. The fractions containing the object compound was gathered and dried under reduced pressure to obtain the object compound (1.74 g).

NMR(CDCl$_3$, δ):1.40(s) and 1.48(s)(9H),2.8–3.2(7H,m), 4.4–4.8(4H,m),5.0–5.6(2H,m),6.4(1H,broad), 6.9–7.8(14H,m),8.3(1H,broad), 9.84(1H, broad)

EXAMPLE 7

Starting compound:

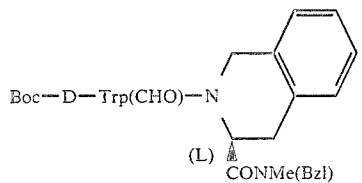

[Intermediate compound:

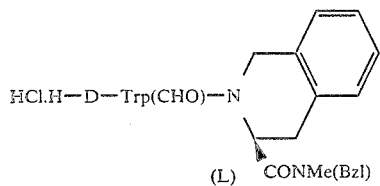

Object compound:

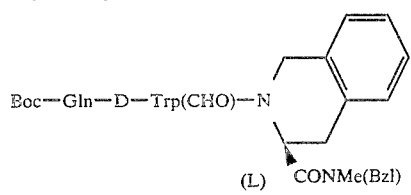

① TFA (20 ml) was added to the mixture of the starting compound (856 mg) and anisole (1.0 ml) under ice-cooling. The reaction mixture was stirred for 15 minutes at the same temperature and then for several minutes at ambient temperature. After condensation under reduced pressure, 4N-HCl/DOX (0.7 ml) was added thereto and condensed again. IPE was added to obtain the powder of the intermediate compound (718 mg).

② Thus obtained intermediate compound (718 mg), Boc-Gln-OH (344 mg) and HOBT (189 mg) were dissolved in DMF (15 ml), and WSC (224 mg) were further added under ice-cooling. The reaction mixture was stirred for 2 hours at the same temperature, and for 1 hour at ambient temperature. After condensing under reduced pressure, the reaction mixture was extracted with ethyl acetate and washed respectively with water, dil. aqueous solution of sodium bicarbonate, dil. hydrochloric acid and brine in turn. The ethyl acetate solution was dried over anhydrous magnesium sulfate and the solvent was distilled off under reduced pressure. The residue was developed for column chromatography of silica-gel (30 g) and eluted with firstly chloroform, and then with a mixture of chloroform-methanol [(100:1.5)→(100:2.5)]. The fractions containing the object compound was condensed under reduced pressure and IPE was added to obtain the powder of the object compound (896 mg).

mp: ~110° C.
IR ( Nujol, δ): 3300–3200,1710, 1660(sh), 1640 cm$^{-1}$
NMR(CDCl$_3$, δ): 1.40(9H,s),1.9–2.3(4H,m), 2.8–3.2(7H,m), 4.1–4.7(4H,m),5.1(1H,m),5.5–5.9(2H,m),6.5 (1H,broad),6.9–7.5(9H,m),7.23(5H, s),8.2(1H, broad),8.83(1H,broad)

EXAMPLE 8

Starting compound:

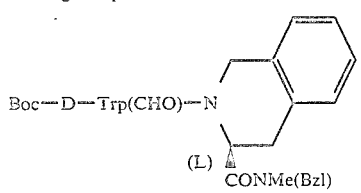

Object compound:

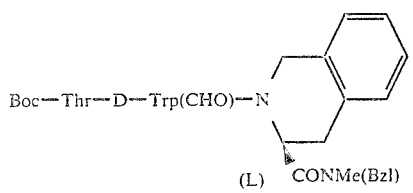

The object compound was obtained from the starting compound in a similar manner to that of the preparative example 7 by using Boc-Thr-Oh in stead of Boc-Gln-OH.

NMR(DMSO-d$_6$, δ):1.03(3H,d,J=7 Hz),1.38(9H,s), 2.65–3.2(7H,m),3.7–4.1(3H,m),4.3–4.8(4H,m), 5.15–5.4(2H,m),6.33(1H,d,J=7 Hz),6.8–7.7(14H,m), 8.2(1H,m), 9.1(1H,broad)

EXAMPLE 9

Starting compound:

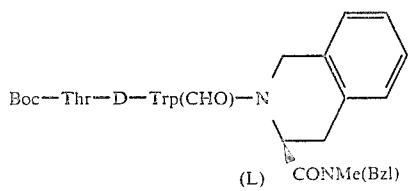

-continued

[Intermediate compound:

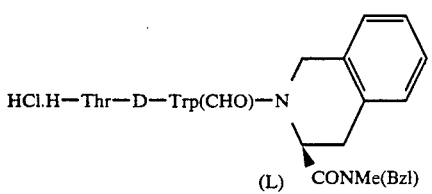

Object compound:

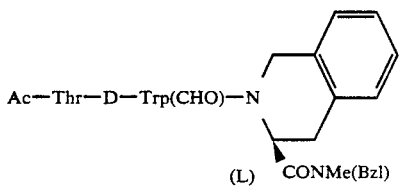

① TFA (20 ml) was added to the mixture of the starting compound (0.88 g) and anisole 1.0 ml) under ice-cooling. The reaction mixture was stirred for 17 minutes at the same temperature and then for 1.15 hour at ambient temperature. After condensation under reduced pressure, 4N-HCl/DOX (0.65 ml) was added thereto and condensed again. IPE was added to obtain the powder of the intermediate compound (682 mg).

② To thus obtained intermediate compound (682 mg), DIPEA (279 mg) was added under ice-cooling, and further added methylene chloride (0.85 ml) solution of AcCl(85 mg). After condensing under pressure, the reaction mixture was extracted with ethyl acetate and washed respectively with water, dil. aqueous solution of sodium bicarbonate, dil. hydrochloric acid and brine in turn. The ethyl acetate solution was dried over anhydrous magnesium sulfate and the solvent was distilled off under reduced pressure. The residue was developed for column chromatography of silica-gel (25 g) and eluted with firstly chloroform, and then with a mixture of chloroform-methanol (100:2.5). The fractions containing the object compound was condensed under reduced pressure and IPE was added to obtain the powder of the object compound (522 mg).

IR (Nujol)=3300, 1710, 1640(8h), 1630 cm⁻¹

NMR(DMSO-d₆, δ):0.90(d) and 1.00(d)(3H, J=7 Hz), 1.87(3H, s),2.6-3.2(7H,m),3.7-4.1(2H,m), 4.1-5.9(6H,m),5.2(1H,m),6.8-7.5(14H,m), 7.7(1H,m),8.1(1H,d,J=8 Hz),9.05(1H,broad)

EXAMPLE 10

Starting compound:

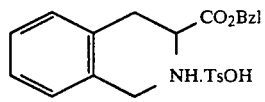

Object compound:

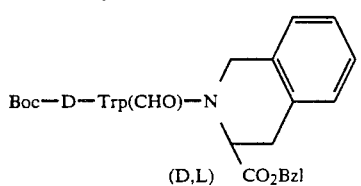

The object compound was obtained from the starting compound in a similar manner to that of example 4.

NMR(CDCl₃, δ):1.19(s) and 1.36(s)(9H),3.1(4H,m), 4.15-4.75(2H,m),4.94(s) and 4.96(s)(2H),5.1-5.6 (2H,m),6.4-6.8(1H,m),6.9-7.5(13H,m),8.7(1H,m), 8.3(1H,broad),8.85(1H,broad)

EXAMPLE 11

Starting compound:

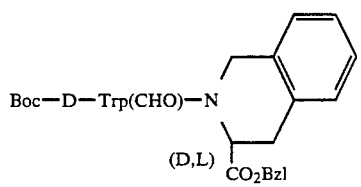

Object compound:

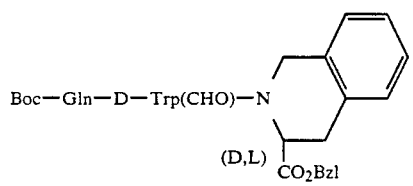

The object compound was obtained from the starting compound by using Boc-Gln-OH in stead of Boc-Thr-OH in a similar manner to that of example 2.

mp: 90°-107° C.

IR (Nujol): 3300, 1740(sh), 1710, 1660 cm⁻¹

NMR(CDCl₃, δ):1.34(s) and 1.40(s)(9H),1.78-2.4(4H,m), 3.0-3.4(4H,m),4-.0-4.6(2H,m),4.7-5.58(3H,m), 5.7-6.35(3H,m),6-.9-7.45(13H,m),7.5-7.8(3H,m), 8.2(1H,m),9.0(1H,broad)

Chemical analysis as C₃₉ H₄₃ N₅ O₈

| Calculated | C 65.99, H 6.11, N 9.87 |
| Found | C 64.94, H 6.27, N 9.39 |

EXAMPLE 12

Starting compound:

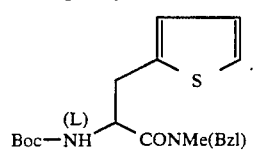

Object compound:

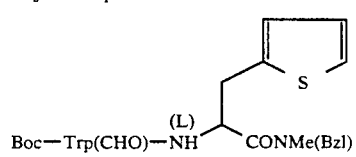

The object compound was obtained from the starting compound in a similar manner to that of example 1.

mp: 86°-88° C.

IR (Nujol): 3300, 1710, 1665, 1620, 1530 cm⁻¹

NMR(DMSO-d₆, δ) 1.29(9H,s),2.74(s) and 2.92(s)(3H), 2.8-3.2(4H,m),4.1-4.7 (3H,m),4.8-5.2(1H,m), 6.7-7.4(11H,m),7.-

45–8.8(2H,m),8.1(1H, broad), 8.5–8.8(1H,m),9.35(1H,-broad)

Chemical analysis as $C_{32}H_{36}N_4O_5S$

| | |
|---|---|
| calculated | C 65.29, H 6.16, N 9.52, S 5.45 |
| Found | C 65.11, H 6.09, N 9.10, S 5.44 |

EXAMPLE 13

Starting compound:

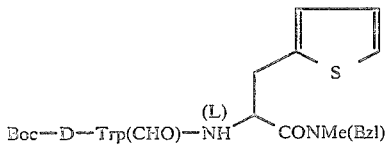

Object compound:

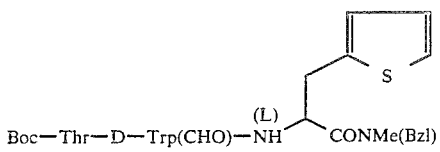

The object compound was obtained from the starting compound by using Boc-Thr-OH in stead of Boc-Gln-OH in a similar manner to that of example 7.

NMR(DMSO-d$_6$, δ):0.89(3H,d,J=6 Hz),1.34(9H, s),2.77 and 2.89(3H, s),2.7–3.4(4H,m),3.6–4.0(2H,m),4.2–5.1 (5H,m),6.26(1H,m),6.7–7.8(13H,m),8.1(1H,m),8.65 (1H,m),9.3(1H,m)

EXAMPLE 14

Starting compound:

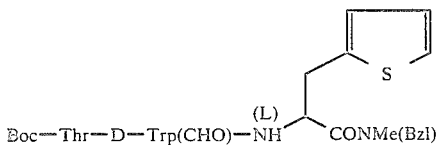

Object compound:

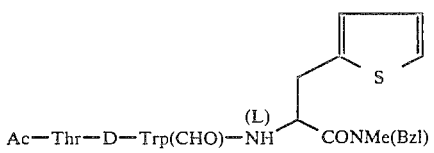

The object compound was obtained from the starting compound in a similar manner to that of example 9.
mp: 191°–192° C.
IR (Nujol): 3300, 1710, 1660(sh), 1645(sh), 1630, 1530 cm$^{-1}$
NMR(DMSO-d$_6$, δ):0.79(3H,d,J=6 Hz),1.86(3H, s),2.77(s) and 2.89(s)(3H),2.75–3.3(4H,m),3.6–3.9(1H,m), 3.96–4.3(1H,m),4.38–5.1(5H,m),6.7–7.8(13H,m), 7.95–8.25(2H,m),8.55–8.8(1H,m),9.2(1H,broad)

Chemical analysis as $C_{33}H_{37}N_5O_6S.\frac{1}{2}H_2O$

| | |
|---|---|
| Calculated | C 61.84, H 6.13, N 10.92 |
| Found | C 62.12, H 5.96, N 10.76 |

EXAMPLE 15

Starting compound: TsOH-H-Tyr-OBzl
Object compound: Boc-D-Trp(CHO)-Tyr-OBzl
The object compound was obtained from the starting compound in a similar manner to that of example 4.
mp: ~167° C.
IR (Nujol): 3480, 3320, 1720, 1690, 1655, 1545, 1530 cm$^{-1}$
NMR(DMSO-d$_6$,δ):1.29(9H, s),2.6–3.2(4H,m),4.2–4.7 (2H,m),5.12(2H, s),6.64(2H,d,J=8 Hz),6.7–7.0 (1H,m),7.03(2H,d,J=8 Hz),7.3–7.9(9H,m),8.0–8.3 (1H,m),8.4–8.6(1H,m),9.22(1H, s),9.4(1H,broad)

Chemical analysis as $C_{33}H_{35}N_3O_7.2H_2O$

| | |
|---|---|
| Calculated | C 63.76, H 6.32, N 6.76 |
| Found | C 63.97, H 6.04, N 6.80 |

EXAMPLE 16

Starting compound: Boc-D-Trp(CHO)-Tyr-OBzl
Object compound: HCl-H-D-Trp(CHO)-Tyr-OBzl
The object compound was obtained from the starting compound in a similar manner to that of example 2 ①.
NMR(DMSO-d$_6$,δ):2.6–3.2(4H,m),4.0–4.3(1H,m),4.4–4.7 (1H,m),5.13(2H, s),6.67(2H, d,J=8 Hz),7.03(2H, d, J=8 Hz),7.2–7.5(7H,m),7.6–7.8(2H,m),8.1–8.5 (4H, broad),9.2–9.5(2H,m),9.40(1H, s)

EXAMPLE 17

Starting compound: HCl-H-D-Trp(CHO)-Tyr-OBzl
Object compound: Boc-Gln-D-Trp(CHO)-Tyr-OBzl
The object compound was obtained from the starting compound by using Boc-Gln-OH in stead of Boc-Thr-OH in a similar manner to that of example 2 ①.
mp: ~203° C. (decomp)
IR (Nujol): 3310, 1695, 1680, 1645,1515 cm$^{-1}$
NMR(DMSO-d$_6$, δ):1.32(9H, s),1.5–2.1(4H,m),2.7–3.1 (4H,m),3.7–4.1(1H,m),4.3–4.9(2H,m),5.09(2H, s), 6.63(2H,d,J=8 Hz),6.7–6.9(1H,m),7.01(2H,d,J=8 Hz), 7.1–7.7(11H,m),7.8–8.3(2H,m),8.5–8.7(1H,m), 9.20(1H, s),9.3(1H,broad)

Chemical analysis as $C_{38}H_{43}N_5O_9 2.\frac{3}{4}H_2O$

| | |
|---|---|
| Calculated | C 62.76, H 6.17, N 9.63 |
| Found | C 62.76, H 6.03, N 9.72 |

EXAMPLE 18

Starting compound: TsOH-H-D-Phe-OBzl
Object compound: Boc-D-Trp(CHO)-D-Phe-OBzl
The object compound was obtained from the starting compound in a similar manner to that of example 4.
mp: ~146° C. (decomp)
IR (Nujol): 3350, 1725, 1680, 1660, 1525 cm$^{-1}$
NMR(DMSO-d$_6$, δ):1.26(9H,s),2.7–3.2(4H,m),4.1–4.8 (2H,m), 5.10(2H, s), 6.8–7.1 ( 1H,m), 7.2–7.5(2H,m), 7.25(5H, s), 7.35( 5H, s), 7.5–7.8(2H,m), 8.2(1H, broad), 8.50(1H, broad d, J=9 Hz ), 9.4 (1H,broad)

Chemical analysis as $C_{33}H_{35}N_3O_6$

| | |
|---|---|
| Calculated | C 69.58, H 6.19, N 7.38 |
| Found | C 69.99, H 6.53, N 7.45 |

EXAMPLE 19

Starting compound: Boc-D-Trp(CHO)-D-Phe-OBzl
Object compound: HCl-H-D-Trp(CHO)-D-Phe-OBzl The object compound was obtained from the starting compound in a similar manner to that of example 2 ①.

IR (Nujol): 1710, 1675, 1550 cm$^{-1}$

NMR(DMSO-d$_6$, δ):2.9–3.5(2H,m),3.0 g(2H:,d,J=7 Hz),4.0–4.4 (1H,m),4.66(1H,q,J=7 Hz),5.09(2H, s),7.1–7.5 (2H,m),7.28(5H, s),7.32(5H, s),7.72 (1H, s),7.8–8.1 (1H,m),8.1–8.4(1H,m),8.42(3H, broad s),9.4(1H, broad),9.41(1H,broad d,J=7 Hz)

EXAMPLE 20

Starting compound: HCl-H-D-Trp(CHO)-D-Phe-OBzl

Object compound: Boc-Gln-D-Trp(CHO)-D-Phe-OBzl

The object compound was obtained from the starting compound by using Boc-Gln-OH in stead of Boc-Thr-OH in a similar manner to that of 2 ②.

mp: 208°–209° C.

IR (Nujol): 3310, 1720, 1690, 1650(broad), 1525 cm$^{-1}$

NMR(DMSO-d$_6$, δ):1.34(9H,s),1.4–2.1(4H,m),2-.8–3.2 (4H,m), 3.7–4.1(1H,m), 4.4–4.8(2H,m), 5.07(2H, s), 6.6–7.0(2H,m), 7.1–7.5(3H,m), 7.27(5H, s), 7.34 (5H,s),7.5–7.8(2H,m),7.9–8.3(2H,m),8.4–8.7 (1H,m),9.3(1H,broad)

Chemical analysis as: C$_{38}$ H$_{43}$ N$_5$ O$_8$

| Calculated | C 65.41, H 6.21, N 10.04 |
| Found | C 66.00, H 6.24, N 10.25 |

EXAMPLE 21

Starting compound:

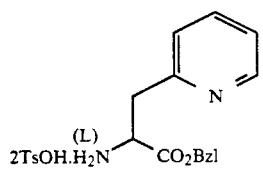

Object compound:

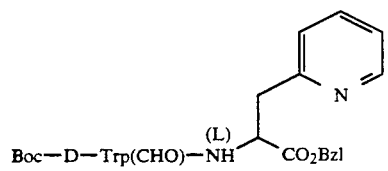

The object compound was obtained from the starting compound in a similar manner to that of example 4.

NMR(DMSO-d$_6$, δ):1.28(9H, s),2.80(2H,m),3.20(2H,m), 4.30(1H,m),4.88(1H,q,J=6 Hz),6.90(1H,d,J=6 Hz), 7.37(5H, s),7.2–7.85(12H,m),8.18(1H, broad), 8.4–8.7(2H,m),9.40(1H,broad)

Chemical analysis as: C$_{32}$ H$_{34}$ N$_4$ O$_6$

| Calculated | C 67.35, H 6.00, N 9.82 |
| Found | C 66.31, H 5.60, N 9.59 |

EXAMPLE 22

Starting compound:

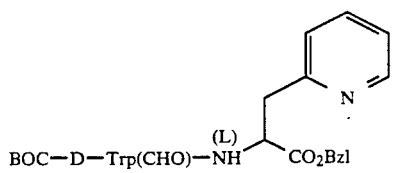

Object compound:

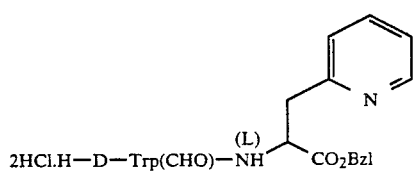

The object compound was obtained from the starting compound in a similar manner to that of example 2 ①.

mp: 217° C. (decomp)

IR (Nujol): 3130, 2700–2500,1740, 1715(sh), 1700(sh), 1690 cm$^{-1}$

NMR(DMSO-d$_6$, δ):3.15(2H,m),3.65(2H,m),4.13(1H,m), 4.95(1H,m),5.21(2H, s),7.45(5H, s),7.72(1H, s),7.8–8.9(8H,m),9.48(1H,broad s),9.90(1H,d,J=8 Hz),10.9 (3H,broad s)

EXAMPLE 23

Starting compound:

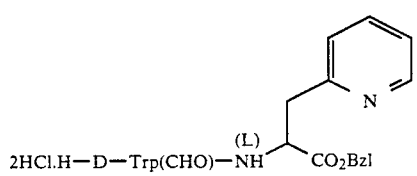

Object compound:

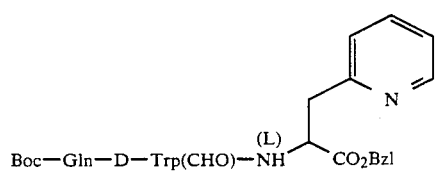

The object compound was obtained from the starting compound by using Boc-Gln-OH in stead of Boc-Thr-OH in a similar manner to that of example 2 ②.

mp: 161°–162° C.

IR (Nujol): 3330,1720, 1690, 1640cm$^{-1}$

NMR(DMSO-d$_6$, δ):1.31(9H, s),1.6(2H,m),1.85(2H,m),2.83 (2H,m),3.15(2H,m),3.95(1H,m),4.7(2H,m),5.11 (2H, s),6.75(2H,m),7.1–7.7(5H,m),7.35(5H, s),8.1 (2H,m),8.48(1H,m),8.7(1H,m),9.28(1H,m)

Chemical analysis as: C$_{37}$ H$_{42}$ N$_6$ O$_8$

| Calculated | C 63.60, H 6.06, N 12.03 |
| Found | C 62.83, H 5.78, N 11.78 |

EXAMPLE 24

Starting compound:

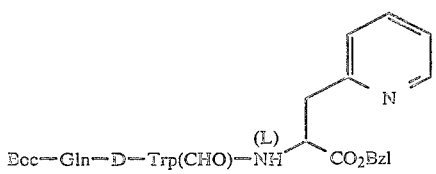

Boc—Gln—D—Trp(CHO)—NH—CH—CO$_2$Bzl (L)

Object compound:

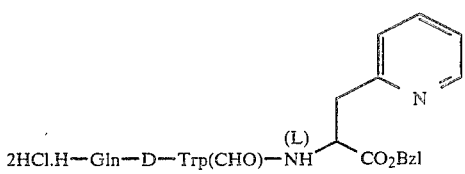

2HCl.H—Gln—D—Trp(CHO)—NH—CH—CO$_2$Bzl (L)

The object compound was obtained from the starting compound in a similar manner to that of example 2 ①.

IR (Nujol): 3450-3200, 2750-2600, 1740, 1710(sh), 1695, 1670 cm$^{-1}$

NMR(DMSO-d$_6$, δ):1.7-2.1(4H,m),2.8-3.2(2H,m),3.6-4.1 (3H,m),4.4-4.7(1H,m),4.9-5.2(1H,m),5.18(2H,s), 6.8-7.0(2H,m),7.32(5H, s),7.3-8.7(12H,m),8.83 (1H,d,J=6 Hz),9.11(2H,m),9.40(1H,broad)

EXAMPLE 25

Starting compound:

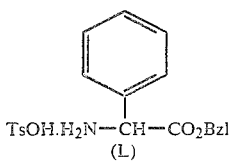

TsOH.H$_2$N—CH—CO$_2$Bzl (L)

Object compound:

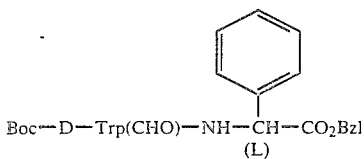

Boc—D—Trp(CHO)—NH—CH—CO$_2$Bzl (L)

The object compound was obtained from the starting compound in a similar manner to that of example 4.

mp: 144°-145° C.

IR (Nujol): 3450, 1740, 1715, 1690, 1650 cm$^{-1}$

NMR(DMSO-d$_6$, δ):1.41(9H,s),3.18(2H,d,J=6 Hz),4.45-4.8 (1H,m),5.12(2H, s),5.58(1H,d,J=6 Hz),5.25 (1H,d,J=6 Hz),6.9-7.8(15H,m),8.1-8.5(1H,m), 8.85(1H, broad)

Chemical analysis as C$_{32}$ H$_{33}$ N$_3$ O$_6$

| | |
|---|---|
| Calculated | C 69.17, H 5.99, N 7.56 |
| Found | C 69.15, H 6.04, N 7.53 |

EXAMPLE 26

Starting compound:

BOC—D—Trp(CHO)—HN—CH—CO$_2$Bzl (L)
(with phenyl group)

Object compound:

BOC—Gln—D—Trp(CHO)—HN—CH—CO$_2$Bzl (L)
(with phenyl group)

The object compound was obtained from the starting compound in a similar manner to that of example 7.

mp: 194°-195° C. (decomp)

IR (Nujol): 3430(Sh), 3310, 3200(Sh), 1710, 1690, 1660(Sh), 1640, 1530, 1170 cm$^{-1}$ NMR(DMSO-d$_6$, δ):1.32(9H,s) 1.47-2.17(4H,m) 2.9-3.1 (2H,m),3.7-4.2(1H,m),4.73-5.1(1H,m),5.18(2H, s), 5.56(1H,d,J=7 Hz),6.7-7.0(2H,m),7.1-7.8(15H,m), 8.0-8.3(1H,m),9.1(1H,d,J=7 Hz),9.3(1H,broad)

Chemical analysis as C$_{37}$ H$_{41}$ N$_5$ O$_8$

| | |
|---|---|
| calculated | C 65.00, H 6.04, N 10.24 |
| Found | C 63.92, H 5.89, N 10.28 |

EXAMPLE 27

Starting compound:

(indane with NH$_2$.HCl and CO$_2$Bzl)

Object compound:

Boc—D—Trp(CHO)—NH (indane) CO$_2$Bzl

The object compound was obtained from the starting compound in a similar manner to that of example 4.

mp: 164°-165° C.

IR (Nujol): 3400, 3320, 1730, 1700,1655 cm$^{-1}$

NMR(CDCl$_3$, δ):1.35(9H,s),2.95-3.91(6H,m),4.0-4.6

NMR(CDCl$_3$, δ): 1.35( 9H,s), 2.95-3.91 (6H,m), 4.0-4.6 (1H,m),5.18(2H,s),6.65(1H,m),7.2-7.7(5H,m),7.15 (4H, s),7.32(5H, s),8.3(1H,broad),8.9(1H,broad)

Chemical analysis as C$_{34}$ H$_{35}$ N$_3$ O$_6$

| | |
|---|---|
| calculated | C 70.21, H 6.06, N 7.22 |
| Found | C 70.23, H 6.17, N 7.17 |

EXAMPLE 28

Starting compound:

-continued

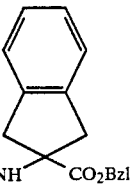

Boc—D—Trp(CHO)—NH  CO$_2$Bzl

Object compound:

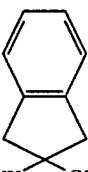

Boc—Gln—D—Trp(CHO)—NH  CO$_2$Bzl

The object compound was obtained from the starting compound in a similar manner to that of example 2.

mp: 162°–164° C.

IR (Nujol): 3300, 1740(sh), 1710, 1680(sh), 1660 cm$^{-1}$

NMR(DMSO-d$_6$, δ):1.31(9H,s),1.5–2.1(4H,m),2.8–4.1 (6H,m),4.5–4.9(2H,m),5.12(2H, s),6.6–7.0(2H,m), 7.1–7.8(5H,m),7.22(4H, s),7.36(5H, s),8.0–8.4 (2H,m),8.8(1H,broad),9.3(1H,broad)

Chemical analysis as C$_{39}$H$_{43}$N$_5$O$_8$

| | |
|---|---|
| calculated | C 65.99, H 6.1, N 9.87 |
| Found | C 65.00, H 6.2, N 9.44 |

EXAMPLE 29

Starting compound: HCl-H-MePhe-NMe(Bzl)

Object compound: Boc-D-Trp(CHO)-MePhe-NMe(Bzl)

The object compound was obtained from the starting compound by using Boc-D-Trp(CHO)-OH in stead of Boc-Thr-OH in a similar manner to that of example 2 ②.

mp: 76°–78° C.

IR (Nujol): 3530, 3220, 1710, 1640cm$^{-1}$

NMR(DMSO-d$_6$, δ):1.24(9H,s),2.5–3.2(4H,m),2.81(3H, s), 2.93(3H, s),4.2–4.8(3H,m),5.5–5.8(1H,m),6.8–7.7 (15H,m),8.1(1H, broad),9.3(1H,broad)

EXAMPLE 30

Starting compound: Boc-D-Trp(CHO)-MePhe-NMe(Bzl)

Object compound: Boc-Thr-D-Trp(CHO)-MePhe-NMe(Bzl)

The object compound was obtained from the starting compound in a similar manner to that of example 2.

mp: 70°–85° C.

IR (Nujol): 3400(broad),1710, 1640cm$^{-1}$

NMR(DMSO-d$_6$, δ):0.87(3H,broad d,J=6 Hz),1.29(s) and 1.34(s)(9H),2.5–3.2(4H,m),2.70(s) and 2.74(s) (3H),2.92(3H,s),3.5–4.1(2H,m),4.2–5.0(4H,m), 5.4–5.7(1H,m),5.9–6.3 (1H,m),6.8–7.6(14H,m), 7.8–8.3(2H,m),9.2(1H,broad)

EXAMPLE 31

Starting compound: Boc-Thr-D-Trp(CHO)-MePhe-NMeBzl

Object compound: Ac-Thr-D-Trp(CHO)-MePhe-NMeBzl

The object compound was obtained from the starting compound in a similar manner to that of example 3.

mp: 85°–90° C.

IR (Nujol): 3320(broad),1710,1640 (broad)cm$^{-1}$

NMR(DMSO-d$_6$, δ):0.85(3H,d,J=6 Hz),1.80(s)and 1.87(s) (3H),2.5–3.2(4H,m),2.75(3H, s),2.95(3H,s),3.6–4.0 (1H,m),4.0–4.35(2H,m),4.35–5.1(3H,m),5.5–5.8 (1H,m),6.8–7.8(15H,m),7.9–8.3(2H,m),9.3(broad s)

Chemical analysis as C$_{36}$H$_{41}$N$_5$O$_6$·2¾H$_2$O

| | |
|---|---|
| calculated | C 66.19, H 6.56, N 10.72 |
| Found | C 66.05, H 6.28, N 10.49 |

EXAMPLE 32

Starting compound: HCl-H-MePhe-OBzl

Object compound: Boc-D-Trp(CHO)-MePhe-OBzl

The object compound was obtained from the starting compound in a similar manner to that of example 4.

mp: 105°–107° C.

IR (Nujol): 3400, 1725, 1715, 1690, 1640, 1520 cm$^{-1}$

NMR(DMSO-d$_6$, δ):1.30(9H, s),2.5–3.4(4H,m),2.85(3H, s), 4.4–4.8(1H,m),4.9–5.4(1H,m),5.17(2H, s),7.0–7.7 (5H,m),7.25(5H, s),7.38(5H, s),7.9–8.4(1H,m), 9.4(1H,broad), Chemical analysis as C$_{34}$H$_{37}$N$_3$O$_6$

| | |
|---|---|
| calculated | C 69.97, H 6.39, N 7.20 |
| Found | C 70.11, H 6.46, N 7.18 |

EXAMPLE 33

Starting compound: Boc-D-Trp(CHO)-MePhe-OBzl

Object compound: HCl-H-D-Trp(CHO)-MePhe-OBzl

The object compound was obtained from the starting compound in a similar manner to that of example 2 ①.

IR (Nujol): 3400(broad),1740, 1710, 1660 cm$^{-1}$

NMR(DMSO-d$_6$, δ):2.5–3.5(4H,m),2.90(3H, s), 4.5–4.8 (1H,m),5.0–5.4(1H,m),5.19(2H,s),7.0–7.8(4H,m), 7.27(5H,s),7.38(5H, s),8.1–8.4(1H,m),8.5(3H, broad s),9.4(1H,broad)

EXAMPLE 34

Starting compound: HCl-H-D-Trp(CHO)-MePhe-OBzl

Object compound: Boc-Gln-D-Trp(CHO)-MePhe-OBzl

The object compound was obtained from the starting compound by using Boc-Gln-OH in stead of Boc-Thr-OH in a similar manner to that of example 2 ②.

mp: 87°–90° C.

IR (Nujol): 3250, 1740, 1710, 1660, 1640, cm$^{-1}$

NMR(DMSO-d$_6$, δ):1.34(9H,s),1.5–2.1(4H,m),2.5–3.4 4H,m),2.81(3H,s),3.8–4.2(1H,m),4.8–5.4(2H,m), 5.16(2H, s),6.75(2H,broad s),7.0–7.7(5H,m),7.24 (5H, s),7.38(5H, s),8.0–8.4(2H,m),9.3(1H,broad)

INDUSTRIAL UTILIZABILITY

Newly provided peptide compound provided in the present invention has a pharmaceutical activity such as anti-tachykinin effect, especialy anti-substance P compound effect, anti-neurochinin A effect, anti-neurochinin B effect, and the like. Accordingly, the present invention provides useful means for therapeuticts or prevention of tachykinin intersitial diseases of human or animals such as respiratpry diseases (e.g., asthma, bronchitis, thiniris cough, expectoration, etc.), optical diseases (e.g., conjunctivitis, vernal conjunctivitis, etc.), dertic diseases (e.g.,(e.g., contact dermatitis, atopic dermatitis, urticaria, other kind of eczematoid deratitis, etc.,) inflammatory diseases (e.g., chronic rheumatism, esteoarthritis, etc.), pain of every kind (e.g., migraine, cephalalgia toothach, cancerous pain, backach, etc.), and the like.

What we claim is:

1. A compound of the general formula:

$$R^1-A^1-(D)-Trp(R^2)-A^2-R^3$$

wherein $R^1$ is hydrogen or acyl;

$R^2$ is acyl;

$R^3$ is ar(lower)alkoxy, N-(lower)alkyl or N-ar(lower)alkylamino $A^1$ is single bond or a bivalent residue derived from an amino acid selected from the group consisting of glutamine, serine, asparagine, glutamic acid, threonine, lysine, histidine, β-aspartic acid, ornithine, glycine, tyrosine, tryptophan, hydroxypurine, pyroglutamic acid, β-alanine, $N^5N^5$-di(lower)alkylglutamine, $N^6$-trihalo(lower)alkoxycarbonyllysine, $N^6$-ar(lower)alkoxycarbonyllysine, $N^\tau$-arenesulfonylhistidine, $N^5$-ar(lower)alkoxycarbonylornithine, $N^6$-haloar(lower)alkoxycarbonyllysine, $O^3$-ar(lower)alkylthreonine, N-loweralkylthreonine, glutamic acid $O^5$-trihalo(lower)alkyl ester, $O^3$-carboxy(lower)alkanoylthreonine; and $A^2$ is a bivalent residue derived from an amino acid selected from the group consisting of glycine, phenylglycine, tyrosine, lysine, D-phenylalanine, methylphenylalanine, 3-pyridylalanine, 3-thienylalanine, 1,2,3,4-tetrahydroisoquinoline-3-carboxylic acid, 2,3-dihydroindene-2-amino-2-carboxylic acid or a pharmaceutically acceptable salt thereof.

2. A pharmaceutical composition comprising a tachykininantagonistic agent of the general formula:

$$R^1-A^1-(D)-Trp(R^2)-A^2-R^3$$

wherein $R^1$ is hydrogen or acyl;

$R^2$ is acyl;

$R^3$ is ar(lower)alkoxy, N-(lower)alkyl or N-ar(lower)alkylamino;

$A^1$ is single bond or a bivalent residue derived from an amino acid selected from the group consisting of glutamine, serine, asparagine, glutamic acid, threonine, lysine, histidine, β-aspartic acid, ornithine, glycine, tyrosine, tryptophan, hydroxypurine, pyroglutamic acid, β-alanine, $N^5N^5$-di(lower)alkylglutamine, $N^6$-trihalo(lower)alkoxycarbonyllysine, $N^6$-ar(lower)alkoxycarbonyllysine, $N^\tau$-arenesulfonylhistidine, $N^5$-ar(lower)alkoxycarbonylornithine, $N^6$-haloar(lower)alkoxycarbonyllysine, $O^3$-ar(lower)alkylthreonine, N-loweralkylthreonine, glutamic acid $O^5$-trihalo(lower)alkyl ester, $O^3$-carboxy(lower)alkanoylthreonine; and $A^2$ is a bivalent residue derived from an amino acid selected from the group consisting of glycine, phenylglycine, tyrosine, lysine, D-phenylalanine, methylphenylalanine, 3-pyridylalanine, 3-thienylalanine, 1,2,3,4-tetrahydroisoquinoline-3-carboxylic acid, 2,3-dihydroindene-2-amino-2-carboxylic acid or a pharmaceutically acceptable salt thereof in admixture with a pharmaceutically acceptable carrier.

* * * * *